United States Patent
Thomas et al.

(10) Patent No.: US 9,365,612 B2
(45) Date of Patent: Jun. 14, 2016

(54) CASPASE INHIBITORS

(75) Inventors: Craig Thomas, Gaithersburg, MD (US); Matthew B. Boxer, Germantown, MD (US)

(73) Assignee: United States of America as represented by the Secretary, Department of Health and Human Services, Washington, DC (US)

( * ) Notice: Subject to any disclaimer, the term of this patent is extended or adjusted under 35 U.S.C. 154(b) by 733 days.

(21) Appl. No.: 13/575,273

(22) PCT Filed: Jan. 27, 2011

(86) PCT No.: PCT/US2011/022744
§ 371 (c)(1),
(2), (4) Date: Jul. 25, 2012

(87) PCT Pub. No.: WO2011/094426
PCT Pub. Date: Aug. 4, 2011

(65) Prior Publication Data
US 2012/0294843 A1 Nov. 22, 2012

Related U.S. Application Data

(60) Provisional application No. 61/299,790, filed on Jan. 29, 2010.

(51) Int. Cl.
*C07D 207/00* (2006.01)
*C07D 295/00* (2006.01)
*C07K 5/062* (2006.01)
*C07K 5/06* (2006.01)

(52) U.S. Cl.
CPC ......... *C07K 5/06034* (2013.01); *C07K 5/06026* (2013.01); *C07K 5/06191* (2013.01)

(58) Field of Classification Search
CPC .. C07D 207/12; C07D 409/04; C07D 205/04; C07D 207/08; C07D 207/10
USPC ............................................ 548/400; 514/18
See application file for complete search history.

(56) References Cited

U.S. PATENT DOCUMENTS

| | | | |
|---|---|---|---|
| 5,656,627 A | 8/1997 | Bemis et al. | |
| 5,874,424 A | 2/1999 | Batchelor et al. | |
| 6,008,217 A | 12/1999 | Batchelor et al. | |
| 6,204,261 B1 | 3/2001 | Batchelor et al. | |
| 6,288,037 B1 | 9/2001 | Talanian et al. | |
| 6,531,474 B1 | 3/2003 | Wannamaker et al. | |
| 6,689,984 B2 | 2/2004 | Maki | |
| 7,205,327 B2 | 4/2007 | Kay et al. | |
| 7,351,702 B2 | 4/2008 | Mortimore et al. | |
| 7,358,273 B2 | 4/2008 | Wannamaker et al. | |
| 7,407,964 B2 | 8/2008 | Charrier et al. | |
| 7,417,029 B2 | 8/2008 | Wannamaker et al. | |
| 7,517,987 B2 | 4/2009 | Golec et al. | |
| 7,652,153 B2 | 1/2010 | Charrier et al. | |
| 7,906,650 B2 | 3/2011 | Golec et al. | |
| 7,960,398 B2 | 6/2011 | Miller et al. | |
| 2002/0058630 A1 | 5/2002 | Charrier et al. | |
| 2005/0004164 A1 | 1/2005 | Caggiano et al. | |
| 2005/0233979 A1 | 10/2005 | Charrier et al. | |
| 2005/0267101 A1 | 12/2005 | Randle | |
| 2009/0023739 A1 | 1/2009 | Charrier et al. | |

FOREIGN PATENT DOCUMENTS

| | | | | |
|---|---|---|---|---|
| AU | WO 2007041775 A1 * | 4/2007 | ........... | A61K 31/131 |
| EP | 0 547 699 | 6/1993 | | |
| EP | 547699 A1 * | 6/1993 | | |
| WO | WO 9924460 A2 * | 5/1999 | | |
| WO | WO 99/47545 | 9/1999 | | |
| WO | WO 99/56765 | 11/1999 | | |
| WO | WO 02/089749 | 11/2002 | | |
| WO | WO 2004/099150 | 11/2004 | | |
| WO | WO 2005/053665 | 6/2005 | | |
| WO | WO 2007/041775 | 4/2007 | | |
| WO | WO 2007041775 A1 * | 4/2007 | | |

OTHER PUBLICATIONS

Smith, P. W., A. B. McElroy, J. M. Pritchard, M. J. Deal, G. B. Ewan, R. M. Hagan, S. J. Ireland, D. Ball, and I. Beresford. "Low-molecular Weight Nuerokinin NK2 Antagonists." Bioorganic and Medicinal Chemistry Letters 3 (5) (1993): 931-36.*
Le, G. T., G. Abbenante, P. K. Madala, H. N. Hoang, and D. P. Fairle. Giang Thanh Le,Giovanni Abbenante,Praveen K. Madala,Huy N. Hoang, and, and David P. Fairlie. "Organic Azide Inhibitors of Cysteine Proteases." Journal of the American Chemical Society 129 (30) (2007): 12396-12397.*
Boxer et al., "A Highly Potent and Selective Caspase 1 Inhibitor that Utilizes a Key 3-Cyanopropanoic Acid Moiety," *ChemMedChem* 5:730-738, Mar. 12, 2010.
Dufour et al., "Peptide Aldehydes and Nitriles as Transition State Analog Inhibitors of Cysteine Proteases," *Biochemistry* 34:9136-9143, 1995.
Hanzlik et al., "Reversible covalent binding of peptide nitriles to papain," *Biochimica et Biophysica Acta* 1035:62-70, 1990.
Le et al., "Organic Azide Inhibitors of Cysteine Proteases," *J. Am. Chem. Soc.* 128:12396-12397, 2006 (available online Sep. 2, 2006).
Mjalli et al., "Phenylalkyl Ketones as Potent Reversible Inhibitors of Interleukin-1β Converting Enzyme," *Bioorganic & Medicinal Chemistry Letters* 3(12):2689-2692, 1993.

(Continued)

*Primary Examiner* — Nyeemah A Grazier
*Assistant Examiner* — Sagar Patel
(74) *Attorney, Agent, or Firm* — Klarquist Sparkman, LLP

(57) ABSTRACT

A compound, or a pharmaceutically acceptable salt or ester thereof, of formula I:

X—W wherein X is a caspase-selective structure and W has the structure of

—NH—CH(Y)(Z)

wherein Y is a structure that can form a reversible covalent bond with a caspase; and
Z is selected from a carboxyl moiety or a carboxylic acid mimetic.

16 Claims, 9 Drawing Sheets

(56) References Cited

OTHER PUBLICATIONS

Nicholson et al., "Identification and inhibition of the ICE/CED-3 protease necessary for mammalian apoptosis," *Nature* 376:37-43, Jul. 6, 1995.

Rano et al., "A combinatorial approach for determining protease specificities; application to interleukin-1β converting enzyme (ICE)," *Chemistry & Biology* 4:149-155, Feb. 1997.

Smith et al., "Low Molecular Weight Neurokinin $NK_2$ Antagonists," *Bioorganic & Medicinal Chemistry Letters* 3(5):931-936, 1993.

Talanian et al., "Substrate Specifics of Caspase Family Protease," *The Journal of Biological Chemistry* 272(15):9677-9682, 1997.

Thornberry et al., "A Combinatorial Approach Defines Specificities of Members of the Caspase Family and Granzyme B," *The Journal of Biological Chemistry* 272(29):17907-17911, 1997.

Wannamaker et al., "(S)-1-((S)-2{[1-(4-Amino-3-chloro-phenyl)-methanoyl]-amino}-3,3-dimethyl-butanoyl)-pyrrolidine-2-carboxylic acid ((2R,3S)-2-ethoxy-5-oxo-tetrahydro-furan-3-yl)-amide (VX-765), an Orally Available Selective Interleukin (IL)-Converting Enzyme/Caspase-1 Inhibitor, Exhibits Potent Anti-Inflammatory Activities by Inhibiting the Release of IL-1β and IL-18," *The Journal of Pharmacology and Experimental Therapeutics* 321(2):509-516, May 1, 2007.

International Search Report and Written Opinion of the International Searching Authority from International Application No. PCT/US2011/022744 dated Mar. 24, 2011.

* cited by examiner

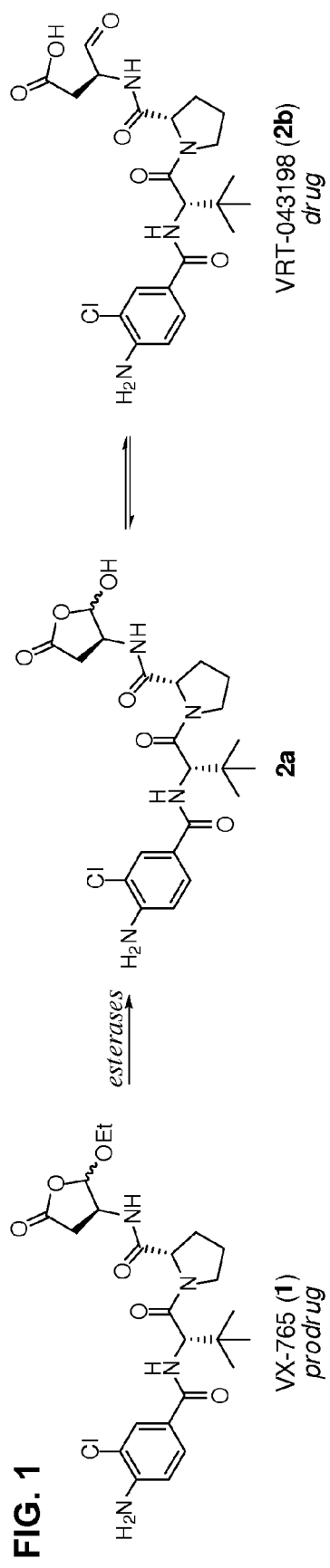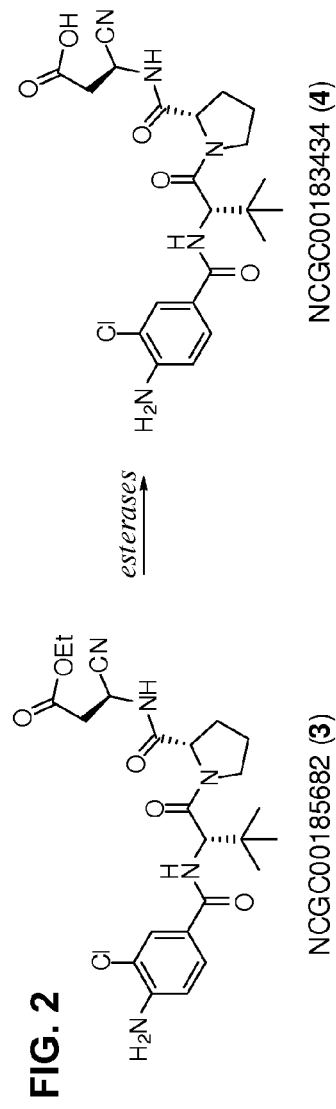
FIG. 1
FIG. 2

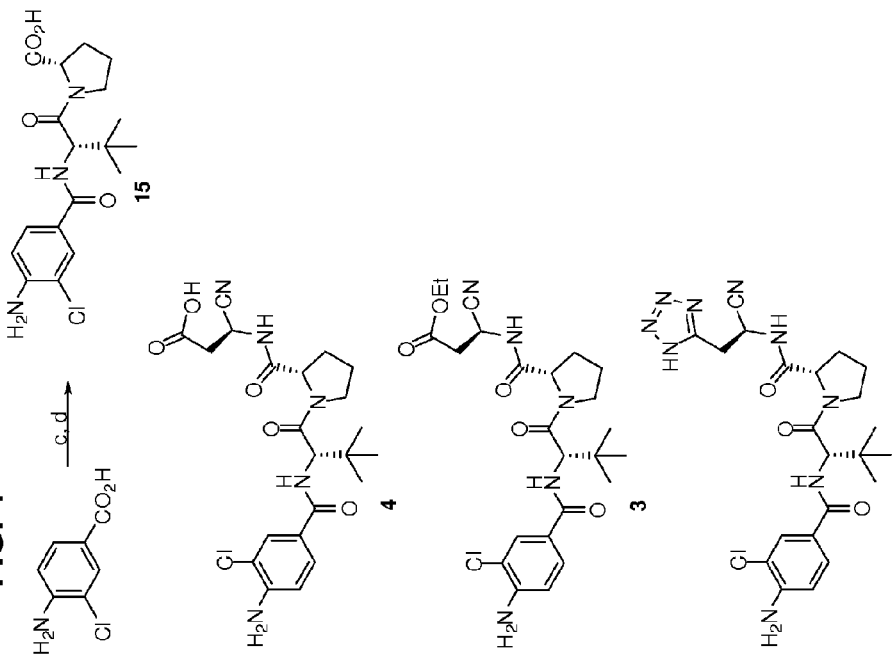
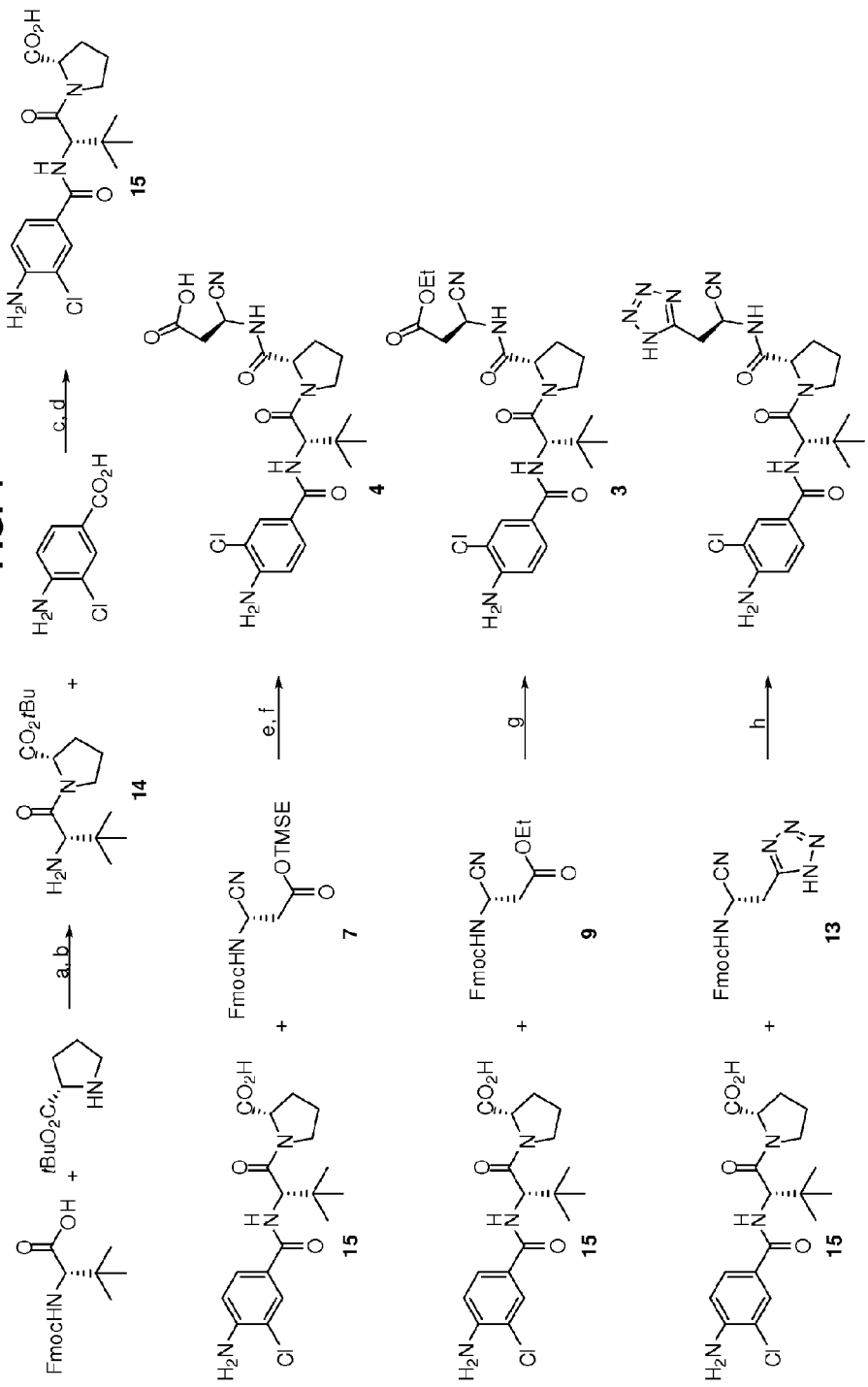
FIG. 4
Scheme 2
Conditions and reagents: (a) EDC, HOBt, DMF, rt, 8 h; (b) DBU, CH$_2$Cl$_2$ (1:1), rt, 4 h (85% over 2 steps); (c) HATU, DIPEA, DMF, rt, 2 h; (d)TFA,CH$_2$Cl$_2$ (71% over 2 steps); (e) DBU, DMF, 5 min. then 15, HATU, DIPEA, DMF, 0 °C, 2h; (f) TBAF, THF, 0 °C (72% over 2 steps); (g) DBU, DMF, 5 min. then 15, HATU, DIPEA, DMF, 0 °C, 2h (91%); (h) DBU, DMF, 5 min. then 15, HATU, DIPEA, DMF, 0 °C, 2h (82%).

FIG. 7

Table 1. IC$_{50}$ values for selected compounds versus caspase panel.

| Compound | Caspase 1 (nM) | Caspase 3 (nM) | Caspase 4 (nM) | Caspase 5 (nM) | Caspase 6 (nM) | Caspase 7 (nM) | Caspase 8 (nM) | Caspase 9 (nM) | Caspase 10 (nM) | Caspase 14 (nM) |
|---|---|---|---|---|---|---|---|---|---|---|
| VRT-043198 (2b) (Drug) | 0.204 | >10000 | 14.5 | 10.6 | >10000 | >10000 | 3.3 | 5.07 | 66.5 | 58.5 |
| 3 (Nitrile ester) | 43.4 | >10000 | >10000 | 1570 | >10000 | >10000 | >10000 | 1610 | >10000 | >10000 |
| 4 (Nitrile acid) | 0.023 | >10000 | 13.8 | 3.60 | >10000 | >10000 | 25.2 | 2.17 | 89.7 | 801 |
| 16 (Nitrile tetrazole) | 2.58 | >10000 | 1380 | 1300 | >10000 | >10000 | >10000 | 91.5 | >10000 | >10000 |
| 20 | 2.16 | >10000 | 114 | 29.0 | >10000 | >10000 | 726 | 297 | 187 | 116 |
| YVAD-CN | 15.0 | ND | 81.7 | 21.3 | ND | ND | 3.82 | 49.2 | 40.4 | 134 |
| Ac-LEHD-CHO (standard) | ND | 3.04 | ND | ND | 122 | 3.54 | ND | ND | ND | ND |
| Ac-DEVD-CHO (standard) | ND | 3.04 | ND | ND | 122 | 3.54 | ND | ND | ND | ND |

[a] Data was generated by Reaction Biology (http://www.reactionbiology.com/). Data is presented as an IC50's using a (Z-LEHD)2-R110 tetrapeptide substrate for caspase 1, 4, 5, 8, 9, 10, 14 and a (Z-DEVD)2-R110 tetrapeptide substrate for caspase 3, 6 and 7. Data represents the results from three separate experiments.

FIG. 9

Table 2. In vitro ADME properties[a] for selected compounds.

| Compound | Caco (A2B)[b] Papp (x10⁻⁶cms⁻¹) | Caco (B2A)[b] Papp (x10⁻⁶cms⁻¹) | Protein Binding[c] fraction unbound | Microsomal Stability[d] CLint (μL/min/mg protein) | Microsomal Stability[d] t1/2 (min) |
|---|---|---|---|---|---|
| VX-765 (2a) (Prodrug) | 0.797 | 32.7 | 0.006 | 0.147 | 9430 |
| VRT-043198 (2b) (Drug) | ND | 0.173 | 0.420 | 6.72 | 206 |
| 3 (Nitrile ester) | 0.445 | 9.59 | 0.071 | 27.4 | 50.7 |
| 4 (Nitrile acid) | 0.144 | 0.060 | 0.431 | 10.3 | 134 |
| 18 (Nitrile tetrazole) | 0.130 | 0.193 | 0.243 | 9.38 | 148 |

[a] Data was generated by Cyprotex (http://www.cyprotex.com/home/). [b] Caco-2 permeability assay over 3 separate experiments with 2 separate internal control groups. Agents were also profiled in the presence of the known Pgp substrate verapamil and data from these experiments highly suggested that 2a and 3 were substrates for efflux by Pgp. [c] Plasma protein binding assays were performed using an equilibrium dialysis method in 100% plasma (profiles versus human and rat plasma were obtained: see the supporting information section for rat plasma binding data). [d] Microsomal stability was profiled alongside internal control compounds, minus NADPH and minus compound (profiles versus human and rat plasma were obtained: see the supporting information section for rat plasma binding data).

CASPASE INHIBITORS

CROSS REFERENCE TO RELATED APPLICATIONS

This is the U.S. National Stage of International Application No. PCT/US2011/022744, filed Jan. 27, 2011, which was published in English under PCT Article 21(2), which in turn claims the benefit of priority of U.S. Provisional Application No. 61/299,790, filed Jan. 29, 2010. The provisional application is incorporated herein in its entirety.

BACKGROUND

Caspases are cysteine proteases so named due to strict specificity for cleaving peptide sequences C-terminal to aspartic acids residues. Currently, 12 caspase isozymes have been identified in humans with numerous reported activities. Caspases are often subcategorized as either pro-apoptotic or pro-inflammatory enzymes. A prominent member of the pro-inflammatory class is caspase 1 (also known as interleukin-converting enzyme or ICE) which is responsible for the proteolytic activation of interleukin (IL)-1β and IL-18. IL-1β and IL-18 are cytokines that play a major role in the immune response and within numerous autoimmune and inflammatory diseases. Caspase 1 is constitutively and inducibly expressed in immune response elements such as T cells, macrophages and neutrophils.

Inhibitors of caspase 1 are sought for intervention strategies within ischemic disorders, Huntington's disease, amyotrophic lateral sclerosis (ALS), rheumatoid arthritis, osteoarthritis, inflammatory bowel disease and sepsis. To date, at least three caspase 1 inhibitors have entered clinical evaluation including Pralnacasan (VX-740), IDN-6556 and VX-765. All three agents are active site inhibitors that act through reversible (Pralnacasan and VX-765) or irreversible (IDN-6556) covalent modification of the catalytic cysteine residue. VX-765 (compound 1) is a prodrug that require esterase cleavage of the 5-ethoxydihydrofuran-2(3H)-one moiety to yield the aldehyde functionality of the drug VRT-043198 (compound 2b) that acts as a potent electrophile for attack by the active site cysteine thiol (see FIG. 1). The remainder of the VX-765 molecule establishes key binding contacts with caspase 1 that enhance the potency of the interaction and confer a modest degree of selectivity. In 2004, Vertex Pharmaceuticals reported that VX-765 had entered a phase II clinical study targeting psoriasis. Subsequent reports on the clinical development of VX-765 have yet to be released.

SUMMARY

Disclosed herein are compounds, and pharmaceutical compositions that include at least one of the compounds, wherein the compounds are caspase inhibitors, especially caspase 1 inhibitors.

In one embodiment, the compound, or a pharmaceutically acceptable salt or ester thereof, has a structure of formula I:

X—W wherein X is a caspase-selective structure and W has the structure of

—NH—CH(Y)(Z)

wherein Y is a structure that can form a reversible covalent bond with a caspase; and Z is selected from a carboxyl moiety or a carboxylic acid mimetic.

In a further embodiment, disclosed herein are compounds, or a pharmaceutically acceptable salt, hydrate or ester thereof, of formula II:

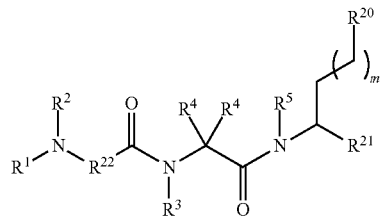

wherein
$R^1$ is H, —C(O)$R^8$, —C(O)C(O)$R^8$, —S(O)$_2R^8$, —S(O)$R^8$, —C(O)O$R^8$, —C(O)N(H)$R^8$, —S(O)$_2$N(H)—$R^8$, —S(O)N(H)—$R^8$, —C(O)C(O)N(H)$R^8$, —C(O)CH=CH$R^8$, —C(O)CH$_2$O$R^8$, —C(O)CH$_2$N(H)$R^8$, —C(O)N($R^8$)$_2$, —S(O)$_2$N($R^8$)$_2$, —S(O)N($R^8$)$_2$, —C(O)C(O)N($R^8$)$_2$, —C(O)CH$_2$N($R^8$)$_2$, —CH$_2R^8$, —CH$_2$-alkenyl-$R^8$, or —CH$_2$-alkynyl-$R^8$;

$R^2$ is H and each $R^6$ is independently —H, an amino acid side chain, or —$R^8$; or $R^2$ and $R^6$ together with the atoms to which they are bound, form a 3 to 7 membered cyclic or heterocyclic ring system;

$R^{22}$ is —C($R^6$)$_2$— or —N($R^6$)—;

$R^3$ is H and each $R^4$ is independently —H, an amino acid side chain, or —$R^8$; or $R^3$ and $R^4$ together with the atoms to which they are bound, form a 3 to 7 membered cyclic or heterocyclic ring system;

$R^5$ is —H;

$R^{21}$ is —CN or —C(O)O$R^9$;

$R^{20}$ is —C(O)O$R^9$, or a heteroaryl;

$R^9$ is —H, alkyl, or —CN; and m is 0 or 1;

provided that at least one of $R^{20}$ or $R^{21}$ includes —CN.

In certain embodiments of formula II, each $R^8$ is independently alkyl, cycloalkyl, aryl, heteroaryl, heterocyclyl, alkylcycloalkyl, alkylaryl, alkylheteroaryl or alkylheterocyclyl. In other embodiments of formula II, $R^1$ is H; $R^6$ is independently —H or an amino acid side chain; and $R^4$ is independently —H or an amino acid side chain.

Also disclosed herein are methods of treating a caspase-mediated condition in a subject that comprise administering to the subject a therapeutically effective amount of at least one of the compounds disclosed herein.

In another aspect, disclosed are methods of inhibiting at least one of caspase 1, 4, 5, 8, 9, 10 or 14 activity in a sample, comprising contacting the sample with at least one of the compounds disclosed herein, whereby the caspase activity is inhibited.

BRIEF DESCRIPTION OF THE DRAWINGS

FIG. 1 is the schematic representation of esterase cleavage of VX-765.

FIG. 2 is the schematic representation of the putative cleavage of a compound disclosed herein.

FIG. 4 is a synthesis scheme for several compounds disclosed herein.

FIG. 7 is a table showing the $IC_{50}$ values of several compounds disclosed herein and a comparative inhibitor.

FIG. 9 is a table showing in vitro ADME properties of several compounds disclosed herein and two comparative inhibitors.

DETAILED DESCRIPTION

Figure 3:
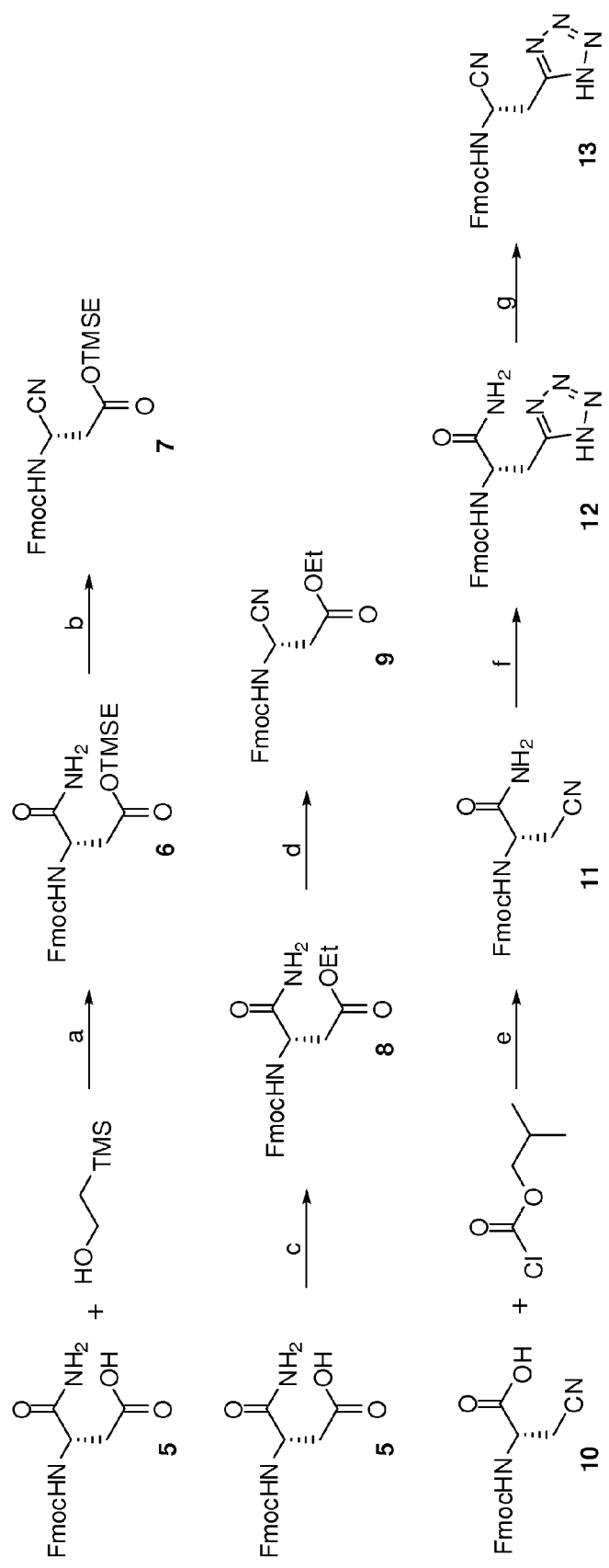
FIG. 3 is a synthesis scheme for synthesizing building blocks for making compounds disclosed herein.

As used herein, the singular terms "a," "an," and "the" include plural referents unless context clearly indicates otherwise. Also, as used herein, the term "comprises" means "includes." It is further to be understood that all nucleotide sizes or amino acid sizes, and all molecular weight or molecular mass values, given for nucleic acids or polypeptides or other compounds are approximate, and are provided for description.

Although methods and materials similar or equivalent to those described herein can be used in the practice or testing of the present disclosure, suitable methods and materials are described below. In addition, the materials, methods, and examples are illustrative only and not intended to be limiting.

To facilitate review of the various examples of this disclosure, the following explanations of specific terms are provided:

The term "acyl" refers group of the formula RC(O)— wherein R is an organic group.

"Administration of" and "administering a" compound should be understood to mean providing a compound, a prodrug of a compound, or a pharmaceutical composition as described herein. The compound or composition can be administered by another person to the subject (e.g., intravenously) or it can be self-administered by the subject (e.g., tablets).

The term "alkoxy" refers to a group of the formula —OR, wherein R is an organic group such as an alkyl group, optionally substituted with an alkenyl, alkynyl, aryl, aralkyl, cycloalkyl, halogenated alkyl, or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms. Alkyl groups may be substituted alkyls wherein one or more hydrogen atoms are substituted with a substituent such as halogen, cycloalkyl, alkoxy, amino, hydroxyl, aryl, or carboxyl.

The term "alkyl amino" refers to alkyl groups as defined above where at least one hydrogen atom is replaced with an amino group.

The term "alkenyl" refers to a hydrocarbon group of 2 to 24 carbon atoms and structural formula containing at least one carbon-carbon double bond.

The term "alkynyl" refers to a hydrocarbon group of 2 to 24 carbon atoms and a structural formula containing at least one carbon-carbon triple bond.

The term "aliphatic" is defined as including alkyl, alkenyl, alkynyl, halogenated alkyl and cycloalkyl groups as described above. A "lower aliphatic" group is a branched or unbranched aliphatic group having from 1 to 10 carbon atoms.

The term "amine" or "amino" refers to a group of the formula —NRR', where R and R' can be, independently, hydrogen or an alkyl, alkenyl, alkynyl, aryl, aralkyl, cycloalkyl, halogenated alkyl, or heterocycloalkyl group described herein.

The term "amide group" or "amido group" is represented by the formula —C(O)NRR', where R and R' independently can be a hydrogen, alkyl, alkenyl, alkynyl, aryl, aralkyl, cycloalkyl, halogenated alkyl, or heterocycloalkyl group described herein.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

The term "aryl" refers to any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be optionally substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

"Carbonyl" refers to a radical of the formula —C(O)—. Carbonyl-containing groups include any substituent containing a carbon-oxygen double bond (C=O), including acyl groups, amides, carboxy groups, esters, ureas, carbamates, carbonates and ketones and aldehydes, such as substituents based on —COR or —RCHO where R is an aliphatic, heteroaliphatic, alkyl, heteroalkyl, hydroxyl, or a secondary, tertiary, or quaternary amine.

A "carboxyl moiety" refers to any moiety or group that includes —C(O)O—. Illustrative carboxyl moieties include carboxylic acid (—C(O)OH); a carboxylate ester (—C(O)OR wherein R is an aliphatic or heteroaliphatic group); a carboxylate salt (—C(O)OM) wherein M is a cation such as Li, Na or K.

The term "co-administration" or "co-administering" refers to administration of the compound disclosed herein with at least one other therapeutic agent within the same general time period, and does not require administration at the same exact moment in time (although co-administration is inclusive of administering at the same exact moment in time). Thus, co-administration may be on the same day or on different days, or in the same week or in different weeks.

A "covalent bond" refers to an interatomic bond between two atoms, characterized by the sharing of one or more pairs of electrons by the atoms. The terms "covalently bound" or "covalently linked" refer to making two separate molecules into one contiguous molecule.

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like. The term "heterocycloalkyl group" is a cycloalkyl group as defined above where at least one of the carbon atoms of the ring is substituted with a heteroatom such as, but not limited to, nitrogen, oxygen, sulfur, or phosphorous.

The terms "halogenated alkyl" or "haloalkyl group" refer to an alkyl group as defined above with one or more hydrogen atoms present on these groups substituted with a halogen (F, Cl, Br, I).

The term "heteroaryl" refers to a mono- or poly-cyclic (e.g., bi-, or tri-cyclic or more) fused or non-fused, radical or ring system having at least one aromatic ring, having from five to ten ring atoms of which one ring atom is selected from S, O and N; zero, one or two ring atoms are additional heteroatoms independently selected from S, O and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroaralkyl" refers to an alkyl residue attached to a heteroaryl ring. Examples include, but are not limited to, pyridinylmethyl, pyrimidinylethyl and the like.

The term "heterocycloalkyl" refers to a non-aromatic 3-, 4-, 5-, 6- or 7-membered ring or a bi- or tri-cyclic group fused of non-fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" is represented by the formula —OH.

The term "hydroxyalkyl" refers to an alkyl group that has at least one hydrogen atom substituted with a hydroxyl group. The term "alkoxyalkyl group" is defined as an alkyl group that has at least one hydrogen atom substituted with an alkoxy group described above.

"Inhibiting" refers to inhibiting the full development of a disease or condition. "Inhibiting" also refers to any quantitative or qualitative reduction in biological activity or binding, relative to a control.

A "mimetic" refers to a chemical entity that contains structural elements capable of mimicking the biochemical or biological action of another chemical entity. For example, in a peptidomimetic the three-dimensional arrangement of the chemical constituents of such peptidomimetic mimics the three-dimensional arrangement of the peptide backbone and component amino acid side chains of another peptide resulting in an agent that is specific and/or selective for target caspase inhibition.

A "peptide" refers to amino acid residues that are joined together through amide bonds. When the amino acids are alpha-amino acids, either the L-optical isomer or the D-optical isomer can be used. The term "peptide" is specifically intended to cover naturally occurring amino acids, as well as those which are recombinantly or synthetically produced. The term "residue" or "amino acid residue" includes reference to a natural, recombinant or synthetic amino acid that may be incorporated into a protein, polypeptide, or peptide. Peptides can be modified by a variety of chemical techniques to produce peptidomimetics having essentially the same activity as the unmodified peptides, and optionally having other desirable properties. For example, carboxylic acid groups of the peptide, whether carboxyl-terminal or side chain, can be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, can be in the form of a pharmaceutically-acceptable acid addition salt, such as the HCl, HBr, acetic, benzoic, toluene sulfonic, maleic, tartaric and other organic salts, or can be modified to $C_1$-$C_{16}$ alkyl or dialkyl amino or further converted to an amide. Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Other peptide modifications include addition and/or deletion and/or substitution of one or more amino acid residue in the peptide chain, and/or replacement of one or more of the amide bond by a non-amide bond, and/or replacement of one or more amino acid side chain by a different chemical moiety, and/or protection of the N-terminus, the C-terminus, or one or more of the side chain by a protecting group, and/or introduction of double bonds and/or cyclization and/or stereospecificity into the amino acid chain to increase rigidity, and/or binding affinity and/or enhance resistance to enzymatic degradation of the peptides.

A "polypeptide" is a polymer in which the monomers are amino acid residues which are joined together through amide bonds.

The term "pharmaceutically acceptable salt or ester" refers to salts or esters prepared by conventional means that include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977). "Pharmaceutically acceptable esters" includes those derived from compounds described herein that are modified to include a hydroxy or a carboxyl group. An in vivo hydrolysable ester is an ester, which is hydrolysed in the human or animal body to produce the parent acid or alcohol. Suitable pharmaceutically acceptable esters for carboxy include $C_{1-6}$ alkoxymethyl esters for example methoxy-methyl, $C_{1-6}$ alkanoyloxymethyl esters for example pivaloyloxymethyl, phthalidyl esters, $C_{3-8}$ cycloalkoxycarbonyloxy $C_{1-6}$ alkyl esters for example 1-cyclohexylcarbonyl-oxyethyl; 1,3-dioxolen-2-onylmethyl esters for example 5-methyl-1,3-dioxolen-2-onylmethyl; and $C_{1-6}$ alkoxycarbonyloxyethyl esters for example 1-methoxycarbonyl-oxyethyl which may be formed at any carboxy group in the compounds.

An in vivo hydrolysable ester containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxy-methoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

It will be appreciated that the compounds described herein may have metal binding, chelating, complex forming properties and therefore may exist as metal complexes or metal chelates.

The term "prodrug" also is intended to include any covalently bonded carriers that release a disclosed compound or a parent thereof in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently claimed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. In particular, ester prodrugs are specifically contemplated herein. Similarly, prodrugs include compounds having an amino or sulfhydryl group functionalized with any group that is cleaved to yield the corresponding free amino or free sulfhydryl group. Examples of prodrugs include, without limitation, compounds having a hydroxy, amino and/or sulfhydryl group acylated with an acetate, formate, or benzoate group.

Protected derivatives of the disclosed compounds also are contemplated. The term "protecting group" or "blocking group" refers to any group that when bound to a functional group prevents or diminishes the group's susceptibility to reaction. "Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. The terms "deprotecting," "deprotected," or "deprotect," as used herein, are meant to refer to the process of removing a protecting group from a compound.

A "therapeutically effective amount" or "diagnostically effective amount" refers to a quantity of a specified agent sufficient to achieve a desired effect in a subject being treated with that agent. For example, this may be the amount of a compound disclosed herein useful in detecting or treating a caspase 1-mediated condition in a subject. Ideally, a therapeutically effective amount or diagnostically effective amount of an agent is an amount sufficient to inhibit or treat the disease without causing a substantial cytotoxic effect in the subject. The therapeutically effective amount or diagnostically effective amount of an agent will be dependent on the subject being treated, the severity of the affliction, and the manner of administration of the therapeutic composition.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease or condition, for example, in a subject who is at risk for a disease such as cancer, particularly a metastatic cancer. A "prophylactic" treatment is a treatment administered to a subject who does not exhibit signs of a disease or exhibits only early signs for the purpose of decreasing the risk of developing pathology.

Particular examples of the presently disclosed agents include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

Some of the compounds described herein may also exist in their tautomeric form.

Compounds and Methods of Making

Disclosed herein are compounds that are caspase inhibitors. In certain embodiments, the caspase inhibitors may inhibit the proteolytic activity of a pro-inflammatory caspase. The caspases inhibited by the disclosed compounds are referred to herein as "target caspases." Such target caspases include caspases 1, 4, 5, 8, 9, 10 and 14. Caspase 1 is a particularly preferred target caspase. For example, inhibition of caspase 1 means inhibition of the proteolytic activation of interleukin (IL)-1β and IL-18.

The caspase inhibitors have the motif: X—W, where X is a caspase-selective structure that is selective for at least one caspase (particularly caspase 1, 4, 5, 8, 9, 10 and/or 14) relative to other cysteine proteases. In certain embodiments, the caspase-selective structure facilitates specificity and/or selectivity among the caspases. In one particular embodiment, the caspase-selective structure is specific for caspase 1. Specificity and/or selectivity of a substrate for a caspase may be determined by biochemical and cell-based assays on related enzymes.

In certain embodiments, X has a structure comprising:

Ar-A²-A¹- wherein Ar is an optionally substituted aryl or optionally substituted heteroaryl; and A¹ and A² are each individually an amino acid residue, or A¹ and A² together form a peptide mimetic.

The caspase-selective structure X may include at least one additional amino acid in addition to A¹ and A². Such additional amino acid(s) may be the same or different compared to the amino acids described below for A¹ and A². However, in certain embodiments X consists only of A¹ and A². The amino acids for A¹ and A² may be natural or unnatural (e.g., recombinant or synthetic) amino acids. A¹ and A² may be the same or different amino acids.

Illustrative amino acids for A¹ and A² may be represented by —N(R¹)—C(R²)(R³)—C(O)— wherein R¹ is H; R² and R³ are each individually selected from H, an optionally substituted alkyl, an optionally substituted cycloalkyl, an optionally substituted heterocycloalkyl, an optionally substituted aryl, or an optionally substituted heteroaryl, or R² and R³ together form a cycloalkyl structure; or R¹ and R² together form an azacyclic structure.

Several specific amino acids for A² are:

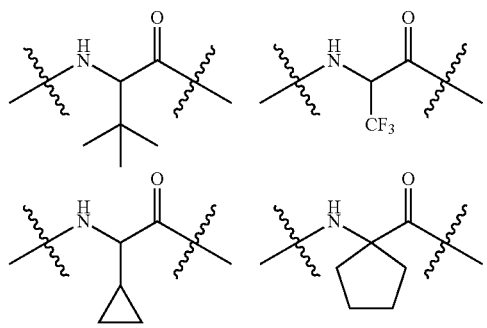

Several specific amino acids for A¹ are:

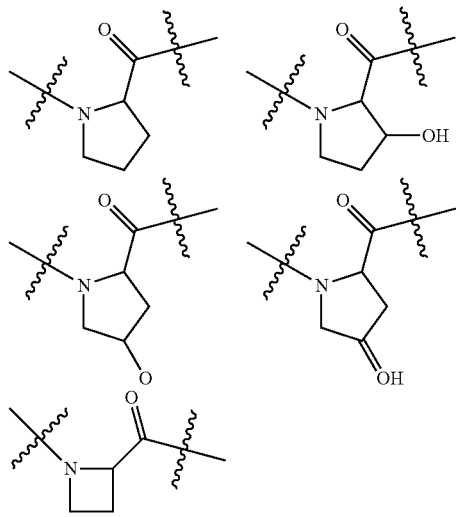

Ar may be an optionally substituted aryl or heteroaryl. The optionally substituted aryl may be a 5-, 6-, or 7-membered single ring such as phenyl or a fused ring such as napthyl or quinolinyl. The optionally substituted heteroaryl may include a heteroatom selected from N, O or S. Illustrative heteroaryl groups include furanyl, pyranyl, pyrroyl, imidazolyl, pyrazolyl, pyridinyl, pyrazinyl, isoindolyl, indoyl, quinolinyl, isothiazolyl, and isoxazolyl. A preferred heteroaryl is pyrindyl. Illustrative substituents include halogen, amino, aminoalkyl (e.g., NMe₂), aminoacyl (e.g., AcHN), halogenated alkyl, alkoxy, and tetrazolyl. The Ar group may include a carbonyl radical (—C(O)—) that bonds to A². In select embodiments, Ar is optionally substituted benzoyl meaning that X has the structure: (optionally substituted)Ph—C(O)-A²-A¹, wherein Ph is phenyl.

Several specific examples for Ar are:

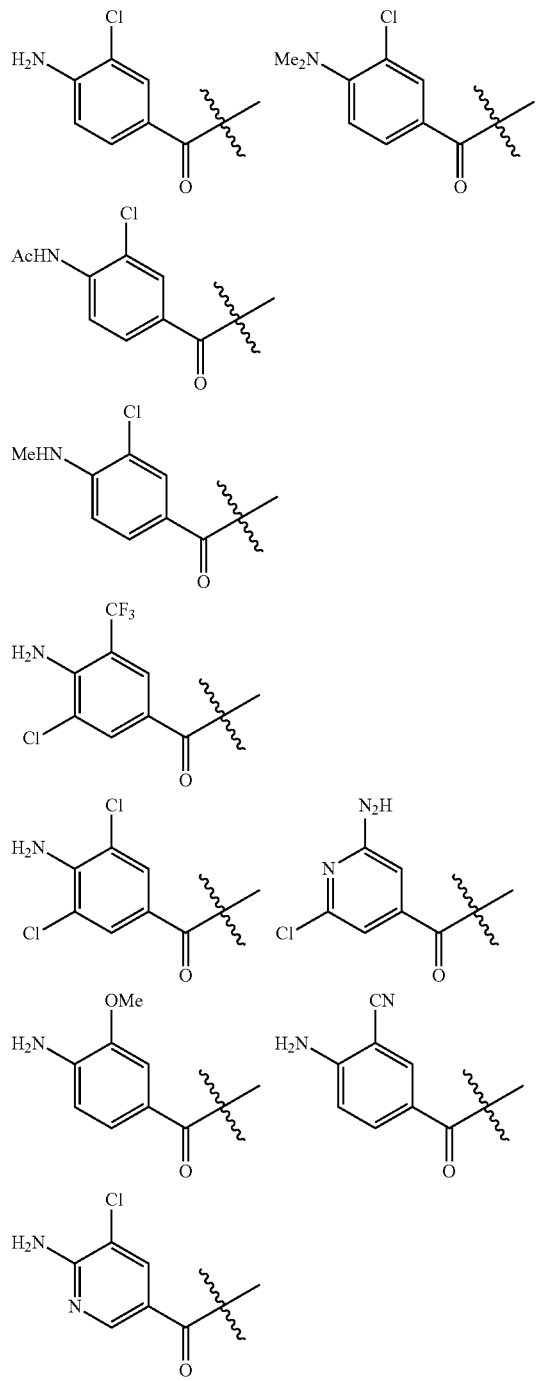
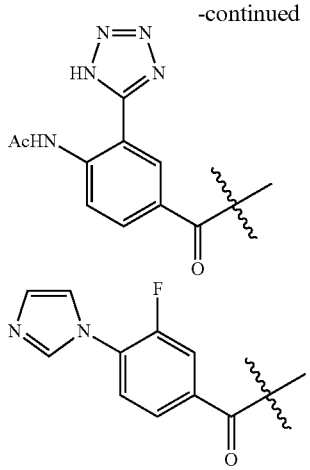

W represents a "warhead" comprising —NH—CH(Y)(Z). The electrophilic warhead reversibly modifies the caspase such that the caspase cannot interact with and cleave a caspase substrate. Although not bound by any theory, it is believed that the novel structure of the warhead disclosed herein enables covalent binding with an active site thiol on the caspase by optimizing hydrophobic and hydrophilic interactions between the inhibitor compound and the caspase, specific intermolecular hydrogen bonding between the inhibitor compound and the caspase, and proper alignment of the enzyme's nucleophilic thiol and the covalent modifier on the inhibitor compound.

Y is a structure that enables the inhibitor compound to form a reversible covalent bond with a caspase (particularly caspase 1, 4, 5, 8, 9, 10 and/or 14). In particular, Y enables formation of a reversible bond with a nucleophilic amino acid residue of the caspase such as a cysteine for caspases. This covalent bond is deemed reversible by the fact the newly formed enzyme-inhibitor bond of the intermediate thioimidate or thioboronate can be broken through hydrolysis or simple reversal of the reaction to generate both free inhibitor and free enzyme. Illustrative Y groups include cyano (—CN), cyano-substituted alkyl (e.g., —CH$_2$CN), boronic acid (—B(OH)$_2$), or boronic acid-substituted alkyl (e.g., —CH$_2$B(OH)$_2$).

Z is a carboxyl moiety or a carboxylic acid mimetic. Illustrative Z groups include cyano (—CN), cyano-substituted alkyl (e.g., —CH$_2$CN), boronic acid (—B(OH)$_2$), boronic acid-substituted alkyl (e.g., —CH$_2$B(OH)$_2$), carboxylic acid (—CO$_2$H), carboxylic acid-substituted alkyl (e.g., —CH$_2$CO$_2$H), carboxylate ester (e.g., —CO$_2$(alkyl), or —CH$_2$CO$_2$(alkyl)), tetrazolyl, tetrazolyl-substituted alkyl (e.g., —CH$_2$-tetrazoyl), or an amido (e.g., —CONH, —CH$_2$CONH(OH), —CH$_2$CONH(OMe) or —CH$_2$CONH(CN)). The carboxylic acid mimetics have a proton with a pKA in the range of 4 to 9, which is near that of carboxylic acid as shown below:

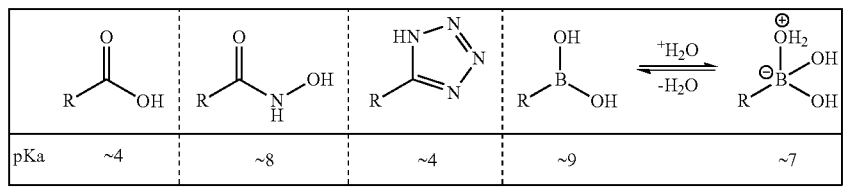

| | | | | | |
|---|---|---|---|---|---|
| pKa | ~4 | ~8 | ~4 | ~9 | ~7 |

According to certain embodiments disclosed herein, $A^2$, $A^1$ and Ar are selected from the specific structures disclosed above; Y is selected from cyano or boronic acid; and Z is selected from —CH$_2$B(OH)$_2$ or —CH$_2$C(O)—O-lower alkyl.

According to certain embodiments disclosed herein, $A^2$ is selected from:

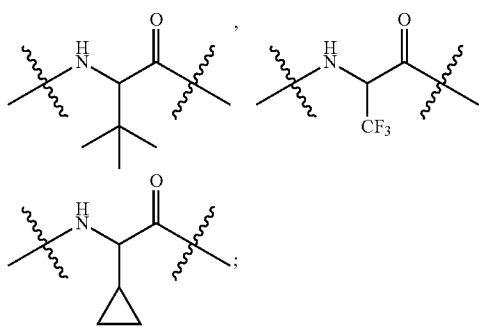

$A^1$ is selected from:

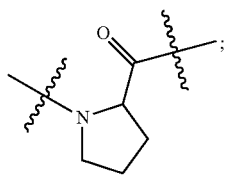 [SMILES: *C(=O)C1CCCN1*]

Ar is selected from:

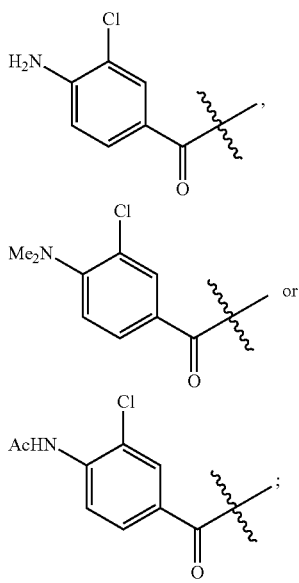

Y is selected from cyano or boronic acid; and Z is selected from —CH$_2$B(OH)$_2$ or —CH$_2$C(O)—O-lower alkyl.

According to certain embodiments disclosed herein, the caspase inhibition agents include a 3-cyanopropanyl moiety incorporated into caspase 1 inhibitor scaffolds. For example, an ethyl-3-cyanopropanoate was incorporated into a VX-765 structure (compound 3; FIG. 2). Carboxylic acid (compound 4; FIG. 2) and tetrazole analogs (compound 16; FIG. 4) were also synthesized. The 3-cyanopropanyl moiety was also introduced onto another known peptide caspase inhibitor -AcN-YVAD-CHO.

According to particular embodiments, the compounds disclosed herein have the structure of formula II:

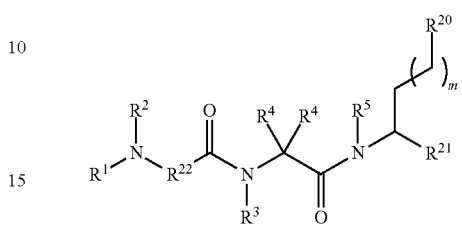

wherein $R^1$ is H, —C(O)R$^8$, —C(O)C(O)R$^8$, —S(O)$_2$R$^8$, —S(O)R$^8$, —C(O)OR$^8$, —C(O)N(H)R$^8$, —S(O)$_2$N(H)—R$^8$, —S(O)N(H)—R$^8$, —C(O)C(O)N(H)R$^8$, —C(O)CH=CHR$^8$, —C(O)CH$_2$OR$^8$, —C(O)CH$_2$N(H)R$^8$, —C(O)N(R$^8$)$_2$, —S(O)$_2$N(R$^8$)$_2$, —S(O)N(R$^8$)$_2$, —C(O)C(O)N(R$^8$)$_2$, —C(O)CH$_2$N(R$^8$)$_2$, —CH$_2$R$^8$, —CH$_2$-alkenyl-R$^8$, or —CH$_2$-alkynyl-R$^8$;

$R^2$ is H and each $R^6$ is independently —H, an amino acid side chain, or —R$^8$; or $R^2$ and $R^6$ together with the atoms to which they are bound, form a 3 to 7 membered cyclic or heterocyclic ring system;

$R^{22}$ is —C(R$^6$)$_2$— or —N(R$^6$)—;

$R^3$ is H and each $R^4$ is independently —H, an amino acid side chain, or —R$^8$; or $R^3$ and $R^4$ together with the atoms to which they are bound, form a 3 to 7 membered cyclic or heterocyclic ring system;

$R^5$ is —H;

$R^{21}$ is —CN or —C(O)OR$^9$;

$R^{20}$ is —C(O)OR$^9$, or a heteroaryl;

$R^9$ is —H, alkyl, or —CN; and m is 0 or 1;

provided that at least one of $R^{20}$ or $R^{21}$ includes —CN.

In more specific examples, the compounds have a formula III:

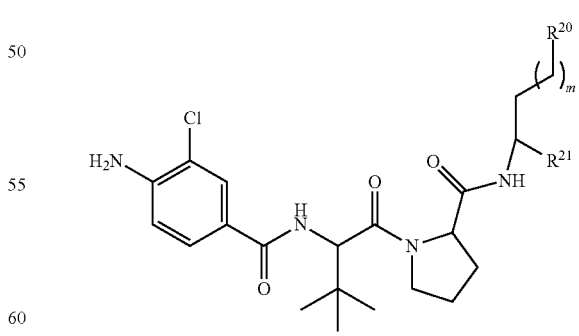

In certain embodiments disclosed herein, the caspase inhibition IC$_{50}$ of the disclosed compounds is less than 100 nM. The compounds may exhibit aqueous solubility of greater than 10 μg/mL, a LogD lower than 5, and a molecular weight of lower than 650 daltons.

Illustrative examples of specific compounds are listed below:
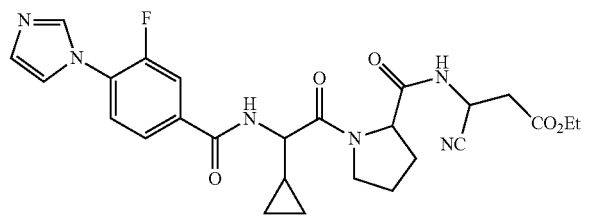
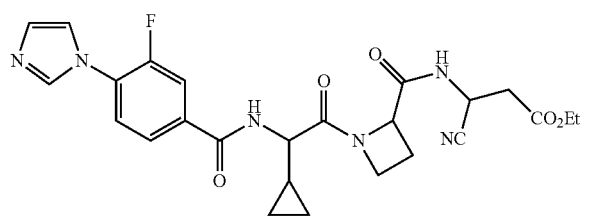
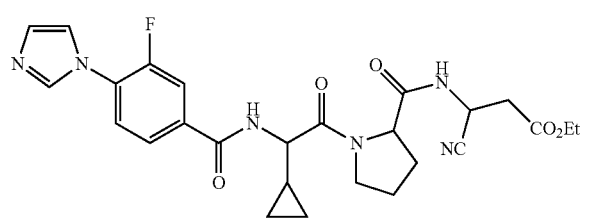
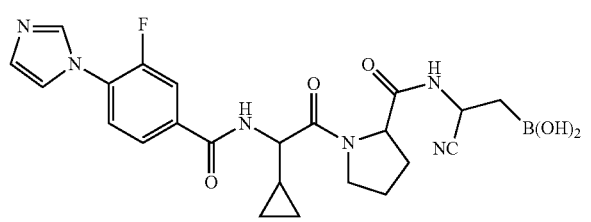
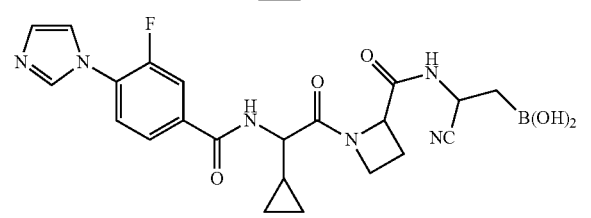
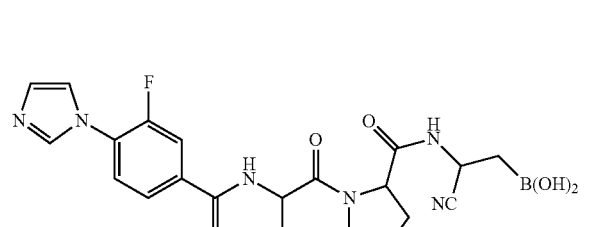
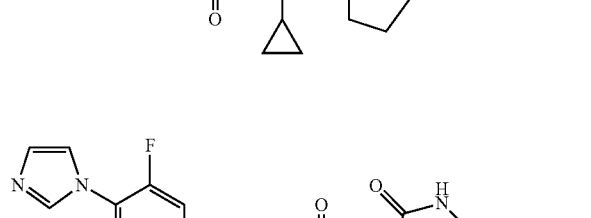
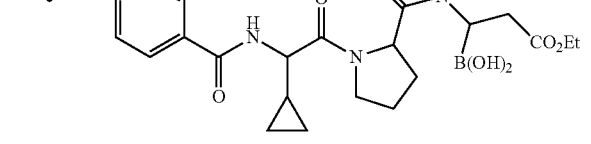
-continued
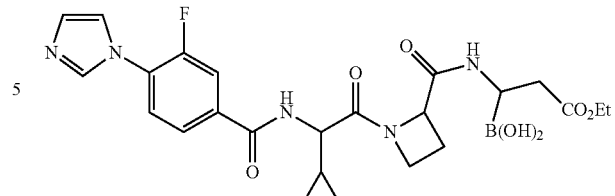
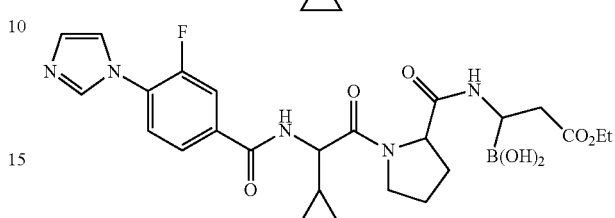
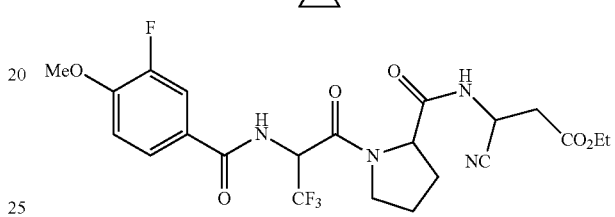
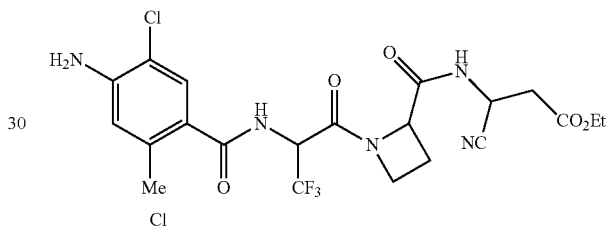
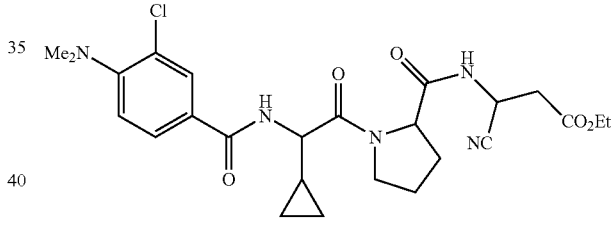
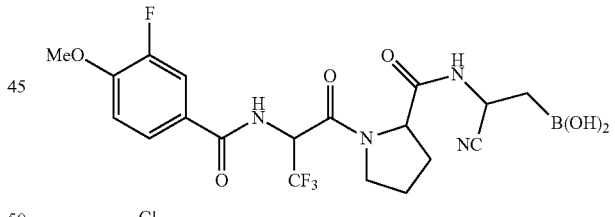
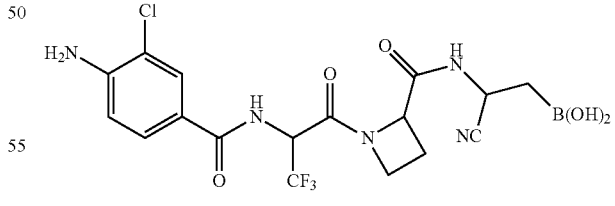
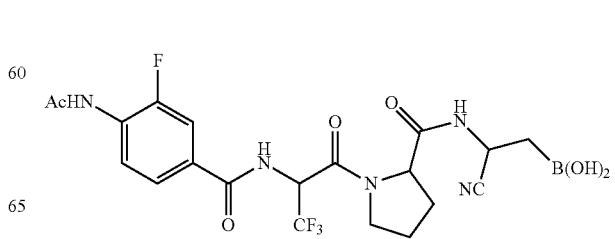

-continued
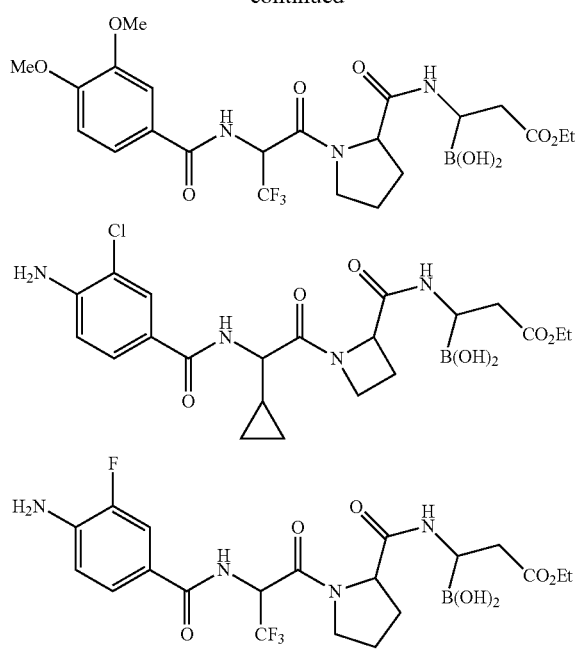
The compounds disclosed herein may be generally synthesized as shown below.
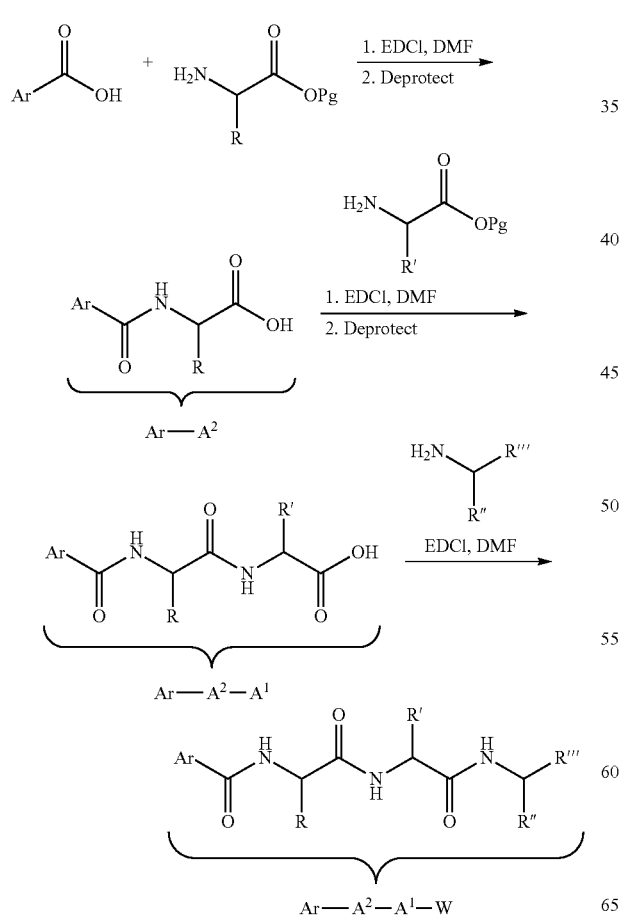
For those compounds that include a boronic acid moiety, the boronic acid building blocks may be synthesized as shown below:
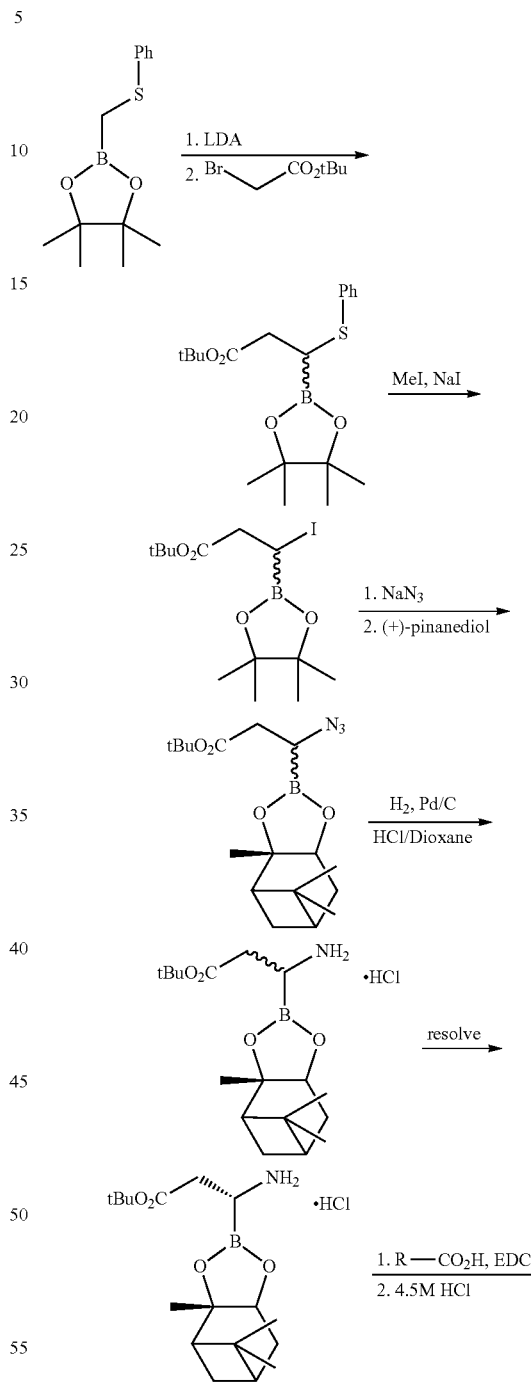
Boronoaspartic Acid Synthesis
Jagannathan, S.; Forsyth, T. P.; Kettner, C. A. J. Org. Chem. 2001, 66, 6375

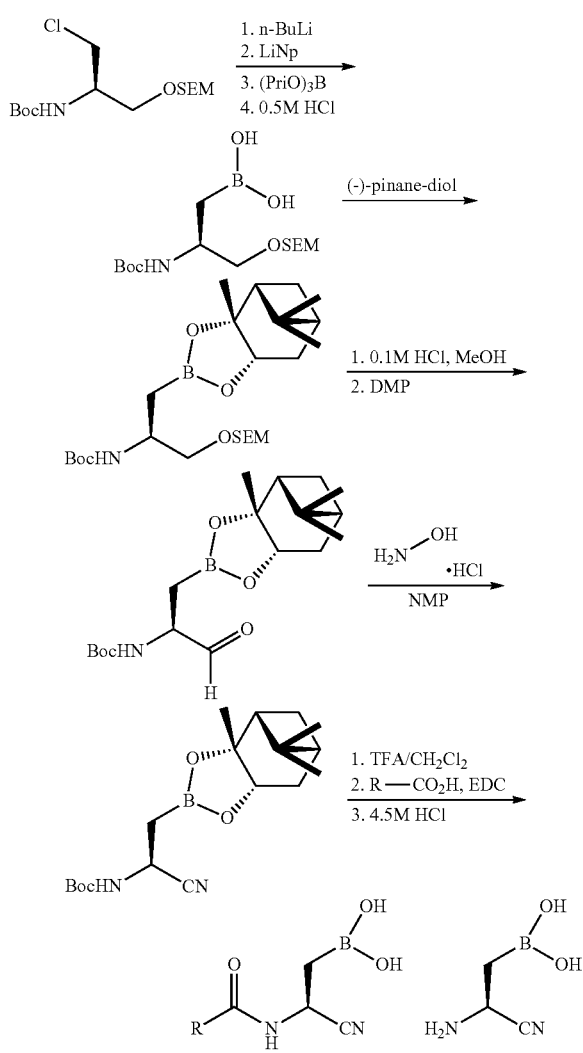

2-Amino-2-Cyanoethylboronic Acid Synthesis
Barfoot, C. W.; Harvey, J. E.; Kenworth, M. N.; KIlburn, J. P.; Ahmed, J.; Taylor, R. J. K. Tetrahedron, 2005, 61, 3403

Compositions and Methods of Use

In one embodiment, the presently disclosed compounds are useful for the treatment of a target caspase-mediated condition. Such conditions include chronic and acute forms of IL-1-, apoptosis-, IL-18-, or IFN-γ-mediated diseases, as well as inflammatory, autoimmune, destructive bone, proliferative, infectious, or degenerative diseases. Such diseases include uveitis, inflammatory diseases, autoimmune diseases, destructive bone disorders, proliferative disorders, infectious diseases, degenerative diseases, necrotic diseases, inflammatory peritonitis, osteoarthritis, acute pancreatitis, chronic pancreatitis, asthma, adult respiratory distress syndrome, glomerulonephritis, rheumatoid arthritis, systemic lupus erythematosus, scleroderma, chronic thyroiditis, Graves'disease, autoimmune gastritis, insulin-dependent diabetes mellitus (Type I), autoimmune hemolytic anemia, autoimmune neutropenia, thrombocytopenia, chronic active hepatitis, myasthenia gravis, inflammatory bowel disease, Crohn's disease, psoriasis, atopic dermatitis, graft vs. host disease, osteoporosis, multiple myeloma-related bone disorder, leukemias and related disorders, myelodysplastic syndrome, acute myelogenous leukemia, chronic myelogenous leukemia, metastatic melanoma, Kaposi's sarcoma, multiple myeloma, sepsis, septic shock, Shigellosis, Alzheimer's disease, Parkinson's disease, cerebral ischemia, myocardial ischemia, myocardial infarction, congestive heart failure, Huntington's disease, atherosclerosis, spinal muscular atrophy, multiple sclerosis, AIDS-related encephalitis, HIV-related encephalitis, aging, alopecia, neurological damage due to stroke, ulcerative collitis, infectious hepatitis, juvenile diabetes, lichenplanus, acute dermatomyositis, eczema, primary cirrhosis, uveitis, Behcet's disease, atopic skin disease, pure red cell aplasia, aplastic anemia, amyotrophic lateral sclerosis, nephrotic syndrome and systemic diseases or diseases with effects localized in the liver or other organs having an inflammatory or apoptotic component caused by excess dietary alcohol intake or viruses, such as HBV, HCV, HGV, yellow fever virus, dengue fever virus, and Japanese encephalitis virus.

IL-1 or apoptosis mediated inflammatory diseases which may be treated include, but are not limited to osteoarthritis, acute pancreatitis, chronic pancreatitis, asthma, and adult respiratory distress syndrome. Preferably the inflammatory disease is osteoarthritis or acute pancreatitis.

IL-1 or apoptosis mediated autoimmune diseases which may be treated include, but are not limited to, glomerulonephritis, rheumatoid arthritis, systemic lupus erythematosus, scleroderma, chronic thyroiditis, Graves'disease, autoimmune gastritis, insulin-dependent diabetes mellitus (Type I), autoimmune hemolytic anemia, autoimmune neutropenia, thrombocytopenia, chronic active hepatitis, myasthenia gravis, multiple sclerosis, inflammatory bowel disease, Crohn's disease, psoriasis, atopic dermatitis and graft vs. host disease. Preferably the autoimmune disease is rheumatoid arthritis, inflammatory bowel disease, Crohn's disease, psoriasis, or atopic dermatitis.

IL-1 or apoptosis mediated destructive bone disorders which may be treated include, but are not limited to, osteoporosis and multiple myeloma-related bone disorder.

IL-1 or apoptosis mediated proliferative diseases which may be treated include, but are not limited to, leukemias and related disorders, such as myelodysplastic syndrome, acute myelogenous leukemia, chronic myelogenous leukemia, metastatic melanoma, Kaposi's sarcoma, and multiple myeloma.

IL-1 or apoptosis mediated infectious diseases which may be treated include, but are not limited to, sepsis, septic shock, and Shigellosis.

IL-1 or apoptosis mediated degenerative or necrotic diseases which may be treated include, but are not limited to, Alzheimer's disease, Parkinson's disease, cerebral ischemia, and myocardial ischemia. Preferably, the degenerative disease is Alzheimer's disease.

IL-1 or apoptosis-mediated degenerative diseases which may be treated include, but are not limited to, Alzheimer's disease, Parkinson's disease, cerebral ischemia, myocardial ischemia, spinal muscular atrophy, multiple sclerosis, AIDS-related encephalitis, HIV-related encephalitis, aging, alopecia, and neurological damage due to stroke.

Other diseases having an inflammatory or apoptotic component may be treated by the disclosed compounds. Such diseases may be systemic diseases or diseases with effects localized in the liver or other organs and may be caused by, for example, excess dietary alcohol intake or viruses, such as HBV, HCV, HGV, yellow fever virus, dengue fever virus, and Japanese encephalitis virus.

IL-18- or IFN-γ-mediated diseases which may be treated include, but are not limited to, inflammatory, infectious, autoimmune, proliferative, neurodegenerative and necrotic conditions.

IL-18- or IFN-γ-mediated inflammatory diseases which may be treated include, but are not limited to osteoarthritis, acute pancreatitis, chronic pancreatitis, asthma, rheumatoid arthritis, inflammatory bowel disease, Crohn's disease, ulcerative collitis, cerebral ischemia, myocardial ischemia and adult respiratory distress syndrome. Preferably, the inflammatory disease is rheumatoid arthritis, ulcerative collitis, Crohn's disease, hepatitis or adult respiratory distress syndrome.

IL-18- or IFN-γ-mediated infectious diseases which may be treated include, but are not limited to infectious hepatitis, sepsis, septic shock and Shigellosis.

IL-18- or IFN-γ-mediated autoimmune diseases which may be treated include, but are not limited to glomerulonephritis, systemic lupus erythematosus, scleroderma, chronic thyroiditis, Graves'disease, autoimmune gastritis, insulin-dependent diabetes mellitus (Type I), juvenile diabetes, autoimmune hemolytic anemia, autoimmune neutropenia, thrombocytopenia, myasthenia gravis, multiple sclerosis, psoriasis, lichenplanus, graft vs. host disease, acute dermatomyositis, eczema, primary cirrhosis, hepatitis, uveitis, Behcet's disease, atopic skin disease, pure red cell aplasia, aplastic anemia, amyotrophic lateral sclerosis and nephrotic syndrome. Preferably, the autoimmune disease is glomerulonephritis, insulin-dependent diabetes mellitus (Type I), juvenile diabetes, psoriasis, graft vs. host disease or hepatitis.

More preferred diseases or conditions which may be treated include rheumatoid arthritis, inflammatory bowel disease, including Crohn's disease and ulcerative colitis, inflammatory peritonitis, amyotrophic lateral sclerosis, septic shock, pancreatitis, traumatic brain injury, organ transplant rejection, osteoporosis, osteoarthritis, asthma, uveitis, psoriasis, Alzheimer's disease, myocardial infarction, congestive heart failure, Huntington's disease, atherosclerosis, atopic dermatitis, or leukemias and related disorders, such as myelodysplastic syndrome or multiple myeloma.

Particularly targeted diseases include ischemic disorders, Huntington's disease, amyotrophic lateral sclerosis (ALS), rheumatoid arthritis, osteoarthritis, inflammatory bowel disease, sepsis, psoriasis, and epilepsy.

One aspect of the present disclosure includes methods for treating a caspase-mediated disorder by administering a therapeutically effective amount of the disclosed compounds to a subject determined to be in need thereof.

Another aspect of the invention disclosed herein is a method of inhibiting target caspase activity in a sample, comprising contacting the sample with one or more of the disclosed compounds. The compounds can be used, for example, to detect the presence of a target caspase in a sample by contacting the sample with the compound and detecting proteolytic cleavage of the compound as an indicator of the presence of the target caspase in the sample. In yet other embodiments, the disclosed compound can be used to isolate the target caspase. For example, a biotinylated form of the compound can be used for affinity purification of the target caspase.

The compounds disclosed herein are also useful as commercial reagents which effectively bind to target caspases including, but not limited to, caspase 1. As commercial reagents, the compounds may be used to block proteolysis of a target peptide in biochemical or cellular assays for target caspases or may be derivatized to bind to a stable resin as a tethered substrate for affinity chromatography applications.

These and other uses which characterize commercial cysteine protease inhibitors will be evident to those of ordinary skill in the art.

Another aspect of the disclosure includes pharmaceutical compositions prepared for administration to a subject and which include a therapeutically effective amount of one or more of the compounds disclosed herein. The therapeutically effective amount of a disclosed compound will depend on the route of administration, the species of subject and the physical characteristics of the subject being treated. Specific factors that can be taken into account include disease severity and stage, weight, diet and concurrent medications. The relationship of these factors to determining a therapeutically effective amount of the disclosed compounds is understood by those of skill in the art.

Pharmaceutical compositions for administration to a subject can include at least one further pharmaceutically acceptable additive such as carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical compositions disclosed herein include those formed from pharmaceutically acceptable salts and/or solvates of the disclosed compounds. Pharmaceutically acceptable salts include those derived from pharmaceutically acceptable inorganic or organic bases and acids. Particular disclosed compounds possess at least one basic group that can form acid-base salts with acids. Examples of basic groups include, but are not limited to, amino and imino groups. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid. In particular, suitable salts include those derived from alkali metals such as potassium and sodium, alkaline earth metals such as calcium and magnesium, among numerous other acids well known in the pharmaceutical art.

Certain compounds include at least one acidic group that can form an acid-base salt with an inorganic or organic base. Examples of salts formed from inorganic bases include salts of the presently disclosed compounds with alkali metals such as potassium and sodium, alkaline earth metals, including calcium and magnesium and the like. Similarly, salts of acidic compounds with an organic base, such as an amine (as used herein terms that refer to amines should be understood to include their conjugate acids unless the context clearly indicates that the free amine is intended) are contemplated, including salts formed with basic amino acids, aliphatic amines, heterocyclic amines, aromatic amines, pyridines, guanidines and amidines. Of the aliphatic amines, the acyclic aliphatic amines, and cyclic and acyclic di- and tri-alkyl amines are particularly suitable for use in the disclosed compounds. In addition, quaternary ammonium counterions also can be used.

Particular examples of suitable amine bases (and their corresponding ammonium ions) for use in the present compounds include, without limitation, pyridine, N,N-dimethylaminopyridine, diazabicyclononane, diazabicycloundecene, N-methyl-N-ethylamine, diethylamine, triethylamine, diisopropylethylamine, mono-, bis- or tris-(2-hydroxyethyl) amine, 2-hydroxy-tert-butylamine, tris(hydroxymethyl)methylamine, N,N-dimethyl-N-(2-hydroxyethyl)amine, tri-(2-hydroxyethyl)amine and N-methyl-D-glucamine. For additional examples of "pharmacologically acceptable salts," see Berge et al., *J. Pharm. Sci.* 66:1 (1977).

Compounds disclosed herein can be crystallized and can be provided in a single crystalline form or as a combination of different crystal polymorphs. As such, the compounds can be provided in one or more physical form, such as different crystal forms, crystalline, liquid crystalline or non-crystalline (amorphous) forms. Such different physical forms of the compounds can be prepared using, for example different solvents or different mixtures of solvents for recrystallization. Alternatively or additionally, different polymorphs can be prepared, for example, by performing recrystallizations at different temperatures and/or by altering cooling rates during recrystallization. The presence of polymorphs can be determined by X-ray crystallography, or in some cases by another spectroscopic technique, such as solid phase NMR spectroscopy, IR spectroscopy, or by differential scanning calorimetry.

The pharmaceutical compositions can be administered to subjects by a variety of mucosal administration modes, including by oral, rectal, intranasal, intrapulmonary, or transdermal delivery, or by topical delivery to other surfaces. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other alternative embodiments, the compound can be administered ex vivo by direct exposure to cells, tissues or organs originating from a subject.

To formulate the pharmaceutical compositions, the compound can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The compound can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The compound can be combined with the base or vehicle according to a variety of methods, and release of the compound can be by diffusion, disintegration of the vehicle, or associated formation of water channels. In some circumstances, the compound is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly(DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly(epsilon-caprolactone), poly(epsilon-aprolactone-CO-lactic acid), poly(epsilon.-aprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

The administration of the compound of the disclosure can be for either prophylactic or therapeutic purpose. When provided prophylactically, the compound is provided in advance of any symptom. The prophylactic administration of the compound serves to prevent or ameliorate any subsequent disease process. When provided therapeutically, the compound is provided at (or shortly after) the onset of a symptom of disease or infection.

For prophylactic and therapeutic purposes, the compound can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the compound (for example, amounts that are effective to elicit a desired immune response or alleviate one or more symptoms of a targeted disease). In alternative embodiments, an effective amount or effective dose of the compound may simply inhibit or enhance one or more selected biological activities correlated with a disease or condition, as set forth herein, for either therapeutic or diagnostic purposes.

The actual dosage of the compound will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the compound for eliciting the desired activity or biological response in the subject. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and formulations of the disclosure is about 0.01 mg/kg body weight to about 20 mg/kg body weight, such as about 0.05 mg/kg to about 5 mg/kg body weight, or about 0.2 mg/kg to about 2 mg/kg body weight.

Dosage can be varied by the attending clinician to maintain a desired concentration at a target site (for example, the lungs or systemic circulation). Higher or lower concentrations can be selected based on the mode of delivery, for example, transepidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth.

The compounds disclosed herein may also be co-administered with an additional therapeutic agent. Such agents include, but are not limited to, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

The instant disclosure also includes kits, packages and multi-container units containing the herein described pharmaceutical compositions, active ingredients, and/or means for administering the same for use in the prevention and treatment of diseases and other conditions in mammalian subjects. Kits for diagnostic use are also provided. In one embodiment, these kits include a container or formulation that contains one or more of the compounds described herein. In one example, this component is formulated in a pharmaceutical preparation for delivery to a subject. The compound is optionally contained in a bulk dispensing container or unit or multi-unit dosage form. Optional dispensing means can be provided, for example a pulmonary or intranasal spray applicator. Packaging materials optionally include a label or instruction indicating for what treatment purposes and/or in what manner the pharmaceutical agent packaged therewith can be used.

EXAMPLES

Compound Synthesis

Figure 5:
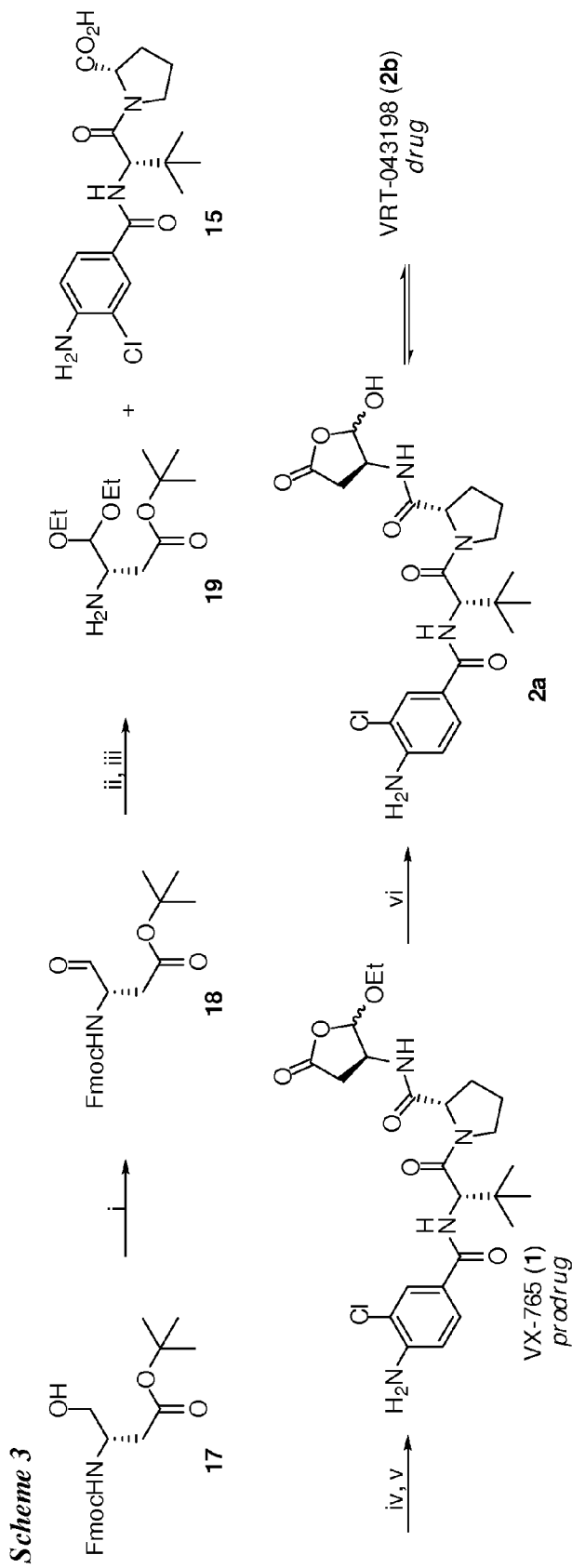
FIG. 5 is a synthesis scheme for making a comparative inhibitor.

Several caspase inhibition agents were synthesized as described below and in FIGS. 3-5. In order to explore both an active and prodrug form of one illustrative molecule, alternative protecting group strategies for the acid side chain were examined (FIG. 3; Scheme 1). Commercially available Fmoc protected D-isoasparagine (5) offered a convenient entry point to both required building blocks. Treatment of 5 with 2-(trimethylsilyl)ethanol, EDC and DMAP in methylene chloride provided the TMSE protected 6 in good yields. Conversion of 6 to nitrile 7 was accomplished by treatment with trifluoroacetic anhydride and Hunig's base. A similar sequence was used to produce the ethyl ester 9. In addition to the ester prodrug and the active cyanopropanoate, it was of interest to explore carboxylic acid mimetics as well. As such, the synthesis of a tetrazole version of the key ethyl-3-cyanopropanoate moiety was accomplished. The previously reported, Fmoc protected (S)-2-amino-3-cyanopropanoic acid (10) was utilized. Sureshbabu, V. V.; Venkataramanarao, R.; Naik, S. A.; Chemakrishnareddy, G. *Tetrahedron Lett.* 2007, 48, 7038-7041. Conversion to the amide 11 was required prior to formation of the tetrazole 12. The amide was created by forming the mixed anhydride followed by treatment with ammonium hydroxide. Tetrazole formation was accomplished via microwave irradiation of the nitrile 11 in the presence of TMS azide and dibutylstannanone. Wittenberger, S. J.; Donner, B. G. *J. Org. Chem.* 1993, 58, 4139-4141. Dehydration to nitrile 13 was accomplished in a manner analogous to 7 and 9.

Synthesis of the trimer core of VX-765 is shown in FIG. 4; Scheme 2. Both Fmoc protected L-tert-leucine and tert-butyl-L-prolinate are commercially available and were easily coupled via treatment with EDC and HOBt. Fmoc removal was effected by treatment with DBU resulting in the protected dimer 14. Coupling of 14 with 4-amino-3-chlorobenzoic acid was accomplished using HATU and Hunig's base in DMF. TFA mediated removal of the tert-butyl group yielded the carboxylic acid 15. A single pot deprotection-coupling sequence was used to generate the desired final products. Treatment of 7, 9 and 13 with DBU in DMF effected deprotection to the free amine, to which was sequentially added 15, Hunig's base and finally HATU to yield the coupled products. The generation of 4 further required TBAF mediated removal of the TMSE group.

Compound 20 was also synthesized as described below:

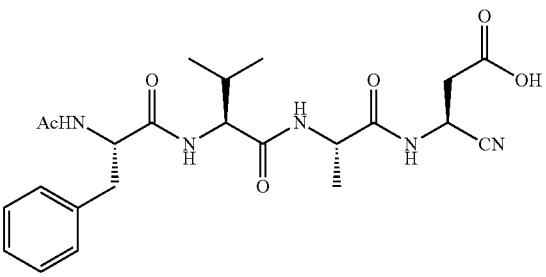

20

(S)-2-((S)-2-((S)-2-acetamido-3-(4-hydroxyphenyl)propanamido)-3-methylbutanamido)propanoic acid (87 mg, 0.22 mmol) and (S)-2-(trimethylsilyl)ethyl 3-amino-3-cyanopropanoate (50 mg, 0.23 mmol) were dissolved in DMF (1.5 mL) and cooled to 0°. Diisopropylethylamine (0.058 mL, 0.33 mmol) was added followed by HATU (101 mg, 0.27 mmol). The reaction was stirred at 0° for 4 hours, diluted with ethyl acetate (5 mL) and quenched with saturated aqueous sodium bicarbonate, washed twice with sodium bicarbonate, once with brine, dried over sodium sulfate and concentrated. Purification by reverse phase chromatography gave 20 as a white powder (131 mg, 67% yield). $^1$H NMR (400 MHz, DMSO-$d_6$) ppm: 8.90-9.29 (b, 1H), 8.63 (d, J=7.2 Hz, 1H), 8.10 (d, J=7.0 Hz, 1H), 7.86-8.04 (m, 1H), 7.62-7.86 (m, 1H), 6.99 (d, J=8.2 Hz, 2H), 6.59 (d, J=8.4 Hz, 2H), 4.83 (dd, J=7.0 Hz, 14.1 Hz, 1H), 4.29-4.51 (m, 1H), 4.08-4.29 (m, 2H), 3.89, 2.65-2.93 (m, 2H), 2.51-2.63 (m, 1H), 1.81-2.09 (m, 1H), 1.72 (s, 3H), 1.18 (d, J=7.0 Hz, 3H), 0.69-0.98 (m, 6H). $^{13}$C NMR (100 MHz, DMSO-$d_6$) ppm: 172.7, 172.6, 171.9, 170.9, 169.6, 156.1, 130.4, 128.5, 119.2, 115.2, 57.6, 54.6, 48.3, 37.4, 36.5, 31.1, 22.9, 19.7, 19.6, 18.4, 18.1. LC/MS: Method 1, retention time: 4.712 min; Method 2, retention time: 3.598 min; HRMS: m/z (M+H$^+$)=473.2277 (Calculated for $C_{23}H_{31}N_5O_6$=473.2274).

VX-765 (1) and VRT-043198 (2b) were also synthesized to compare them to the novel compounds disclosed. In 2008, Magdziak and coworkers reported a synthesis of VX-765 (1) that relied upon a well engineered Pd catalyzed coupling of the vinyl bromide of the ethoxyfuranone and the amide of a Cbz-protected proline amide. Tanoury, G. J.; Chen, M.; Dong, Y.; Forslund, R. E.; Magdziak, D. *Org. Lett.* 2008, 10, 185-188. It was convenient to begin with the orthogonally protected D-β-homoserine 17 which is transformed to the aldehyde 18 via the Parikh-Doering oxidation in good yield (FIG. 5; Scheme 3). Parikh, J. P.; Doering, W. E. *J. Am. Chem. Soc.* 1967, 89, 5505-5507. Conversion to the diethyl acetal and removal of the Fmoc protecting group provided the free amine 19 in modest yields over 2 steps. Standard coupling of 19 and 15 with HATU and Hunig's base was followed by treatment with TFA in dry methylene chloride to generate the 5-ethoxydihydrofuranone present in VX-765 (1). Generation of hemiketal 2a/VRT-043198 (2b) was accomplished by treating 1 with HCl in a THF/water mixture.

Results

Figure 6:
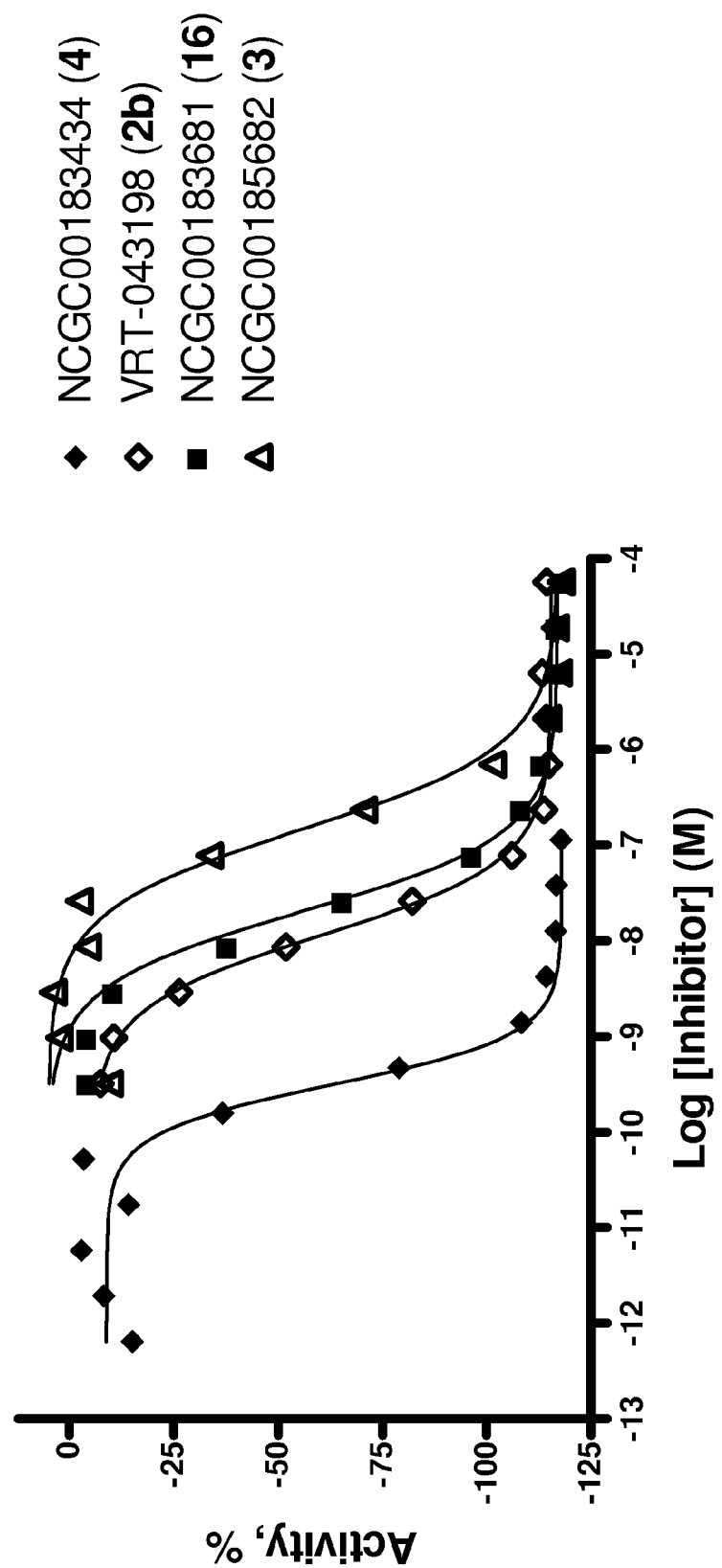
FIG. 6 is a graph depicting caspase 1 inhibition activity of several compounds disclosed herein and a comparative inhibitor.

Each agent's inhibitory capacity versus caspase 1 was evaluated. A well established protocol was utilized whereby caspase 1 activity is measured utilizing 2 nM enzyme in the presence and absence of compound and a caged fluorescent peptide substrate (Ac-LEHD-AMC). Wannamaker et al, Journal of Pharmacology and Experimental Therapeutics, 2007, 321, 509-516. The compounds were examined across a titration series (0.325 nM→57.5 µM) and data was recorded via fluorescence detection following an incubation period of 20 minutes at room temperature. We examined VRT-043198 (2b), NCGC00185682 (3), NCGC00183434 (4) and the tetrazole NCGC00183681 (16) and the results are displayed in FIG. 6. VRT-043198 (2b) was confirmed as a potent caspase 1 inhibitor with an $IC_{50}$ value of 11.5 nM. NCGC00183434 (4) which contains the cyanopropanoate moiety was found to inhibit caspase 1 with an impressive $IC_{50}$ value of 0.316 nM. The ethyl ester NCGC00185682 (3) and tetrazole NCGC00183681 (16) retained impressive potencies versus caspase 1 ($IC_{50}$=144.7 nM and $IC_{50}$=20.4 nM, respectively).

Having established that the compounds (3), (4) and (16) are potent inhibitors of caspase 1, the selectivity of these agents was examined. Randle and coworkers have reported the Ki values of VRT-043198 (2b) versus caspases 1, 3, 4, 6, 7, 8 and 9 and versus granzyme B, cathepsin B and tyrpsin. Wannamaker, W.; Davies, R.; Namchuk, M.; Pollard, J.; Ford, P.; Ku, G.; Decker, C.; Charifson, P.; Weber, P.; Germann, U. A.; Kuida, K.; Randle, J. C. R. *J. Pharmacol. Exp. Ther.* 2007, 321, 509-516. This report presents evidence that VRT-043198 (2b) is nearly equipotent versus caspases 1 and 4 (Ki=<1 nM) and modestly potent versus caspases 8, 6 and 9 (100 nM, 560 nM and 1030 nM, respectively) while possessing little activity versus the remaining targets. VRT-043198 (2b), NCGC00185682 (3), NCGC00183434 (4) and NCGC00183681 (16) were entered within a commercial panel of caspases offered by Reaction Biology Corporation. The results are shown in FIG. 7, Table 1. This data confirmed the potent inhibitory capacity of VRT-043198 (2b) versus caspase 1 ($IC_{50}$=0.204 nM), however the $IC_{50}$ values found versus caspase 4 ($IC_{50}$=14.5 nM) and caspase 8 ($IC_{50}$=3.3 nM) differed slightly from the reported values. The results versus caspase 6 ($IC_{50}$=>10,000 nM) and caspase 9 ($IC_{50}$=5.07 nM) were significantly different from those reported by Randle and coworkers. The results for NCGC00183434 (4) demonstrated an impressive potency versus caspase 1 ($IC_{50}$=0.023 nM) and a similar selectivity profile as VRT-043198 (2b). The only prominent divergence between the selectivity profiles of NCGC00183434 (4) and VRT-043198 (2b) was a sharp drop in the ability to inhibit caspase 14 ($IC_{50}$=801 nM and $IC_{50}$=58.5 nM, respectively). The caspase 1 inhibition data generated in this panel for NCGC00185682 (3) and NCGC00183681 (16) mirrored the data generated in our caspase 1 assay with reported $IC_{50}$ values of 43.4 nM and 2.58 nM, respectively. A particularly interesting aspect of these molecules was the high selectivity for caspase 1. NCGC00183681 (16) registered an $IC_{50}$ value of 91.5 nM versus caspase 9. All other activities were about the 1 µM threshold. The agent YVAD-CN (20) was also profiled and the results clearly demonstrate that cyanopropanoates represent a general moiety for reversible, covalent modification of caspases.

Figure 8:
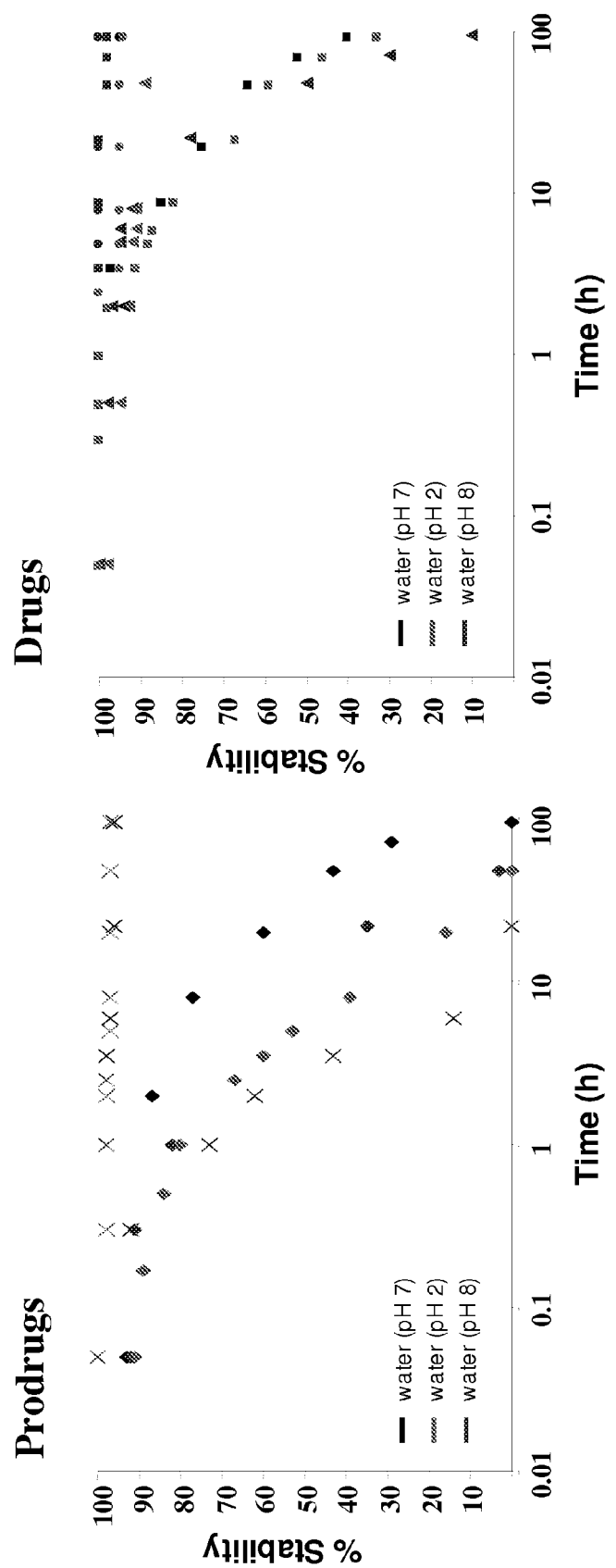
FIG. 8 is two graphs depicting aqueous stability of several compounds disclosed herein and a comparative inhibitor.

In order to evaluate the agent's stability profile, VX-765 (1), VRT-043198 (2b), NCGC00185682 (3), NCGC00183434 (4) and NCGC00183681 (16) were examined within an aqueous degradation study at neutral (pH 7) acidic (pH 2) and basic (pH 8) conditions. The study was conducted by monitoring the degradation of each agent by LCMS analysis at various time points over 96 hours (FIG. 8). The prodrug VX-765 (1) showed moderate degradation in water with over 50% of the compound decomposed after 48 hours. This degradation was amplified in both basic and acidic conditions. Conversely, the active agent VRT-043198 (2b) was very stable in both water and acidic conditions and its degradation at pH 8 was moderate. The potent NCGC00183434 (4) was exceedingly stable in basic conditions and its stability in neutral and acidic conditions was moderate to good (degradation of 50% in both conditions after 72 hours). The ethyl ester NCGC00185682 (3) was exceptionally stable in neutral and acidic conditions (no degradation noted), however, it was fully degraded in basic conditions after 22 hours (presumably due to saponification of the ester). Finally, the tetrazole NCGC00183681 (16) was found to be resistant to degradation in all conditions. Interestingly, this data highly suggests that VX-765 (1) will have a short half-life as an oral agent due to its instability in acidic conditions such as those found in the gastric environment (40% degradation after 3.5 hours at pH 2). In contrast, this data highly suggests that NCGC00185682 (3) and NCGC00183681 (16) will be suitable reagents for all manner of examinations (cell based and in vivo studies) and even the highly active NCGC00183434 (4) will persist beyond 24 hours.

Given the aqueous stability of these new agents, selected ADME properties for chosen compounds were also examined. VX-765 (1), VRT-043198 (2b), NCGC00185682 (3), NCGC00183434 (4) and NCGC00183681 (16) were evaluated for a profile of bi-directional Caco-2 permeability, plasma protein binding (both human and rat) and microsomal stability (both human and rat) studies (FIG. 9, Table 2). All agents possessed poor A to B permeability, however, the prodrug VX-765 (1) and the ester NCGC00185682 (3) had moderately better levels. The high B to A levels reported for VX-765 (1) and NCGC00185682 (3) highly suggested an active transport mechanism and a control experiment with verapamil confirmed that these agents are substrates for Pgp efflux. Unsurprisingly, the free acids VRT-043198 (2b) and NCGC00183434 (4) and the tetrazole NCGC00183681 (16) had significantly higher free fractions in both human and rat protein binding assays relative to the more hydrophobic prodrug VX-765 (1) and ethyl ester NCGC00185682 (3). The clearance rates (Clint) and t ½ for VRT-043198 (2b), NCGC00185682 (3), NCGC00183434 (4) and NCGC00183681 (16) were all moderate. The ester NCGC00185682 (3) was noted to possess a slight degree of degradation in liver microsomes without NADPH as a cofactor suggesting a non-enzyme related degradation mechanism. The prodrug VX-765 (1) possessed minimal ability to be metabolized by liver microsomes and at ½ of >9400 minutes.

Figure 10:
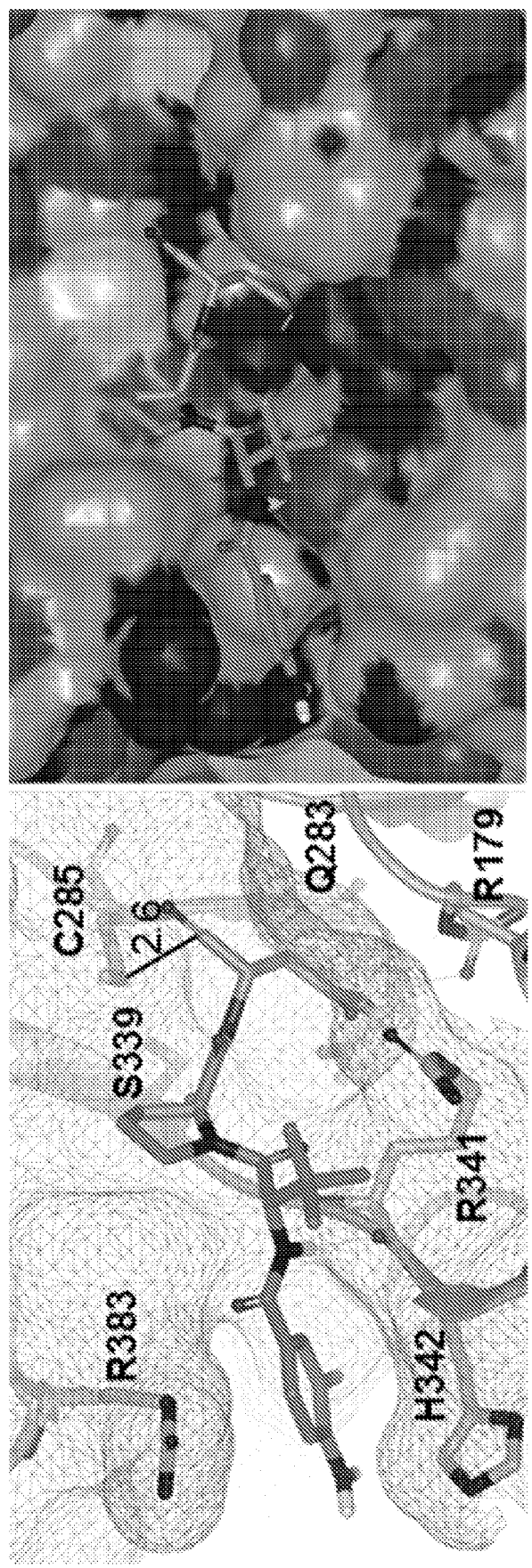
FIG. 10 is a molecular model of the binding of a compound disclosed herein to caspase 1.

The binding mechanism of the compounds was also examined through molecular modeling. Several crystal structures of caspase 1 exist including structures with reversible and non-reversible inhibitors (PDB codes: 1BMQ, 1IBC, 1ICE, 1RWK, 1RWM, 1RWN, 1RWO, 1RWP, 1RWV, 1RWW, 1RWX, 1SC1, 1SC3, 1SC4, 2FQQ, 2H48, 2HBQ, 2HBR, 2HBY, 2HBZ, 2FQR, 2FQS, 2FQU, 2FQZ). 2HBQ was identified as the best template for NCGC00183434 (4)(2HBQ is a co-crystal of caspase 1 and Z-VAD-FMK). The presumption of a covalent reversible mechanism of inhibition was applied when building a model for binding of NCGC00183434 (4). The nitrile carbon was therefore held at a proximal distance (2.6 Å) from the catalytic cysteine residue (C285) by constraint docking and flexibility was granted to the remainder of the small molecule to achieve an optimal binding pose using FRED. The results are shown in FIG. 10 and demonstrate complementarity between the peptidic fragment of 4 and the peptide binding domain of caspase 1.

Illustrative embodiments of the compounds, compositions and methods disclosed herein are described below in the following numbered paragraphs:

1. A compound, or a pharmaceutically acceptable salt or ester thereof, of formula I:

X—W wherein X is a caspase-selective structure and W has the structure of

—NH—CH(Y)(Z)

wherein Y is a structure that can form a reversible covalent bond with a caspase; and Z is selected from a carboxyl moiety or a carboxylic acid mimetic.

2. The compound of paragraph 1, wherein X has a structure comprising:

Ar-A$^2$-A$^1$- wherein Ar is an optionally substituted aryl or optionally substituted heteroaryl; and A$^1$ and A$^2$ are each individually an amino acid residue, or A$^1$ and A$^2$ together form a peptide mimetic.

3. The compound of paragraph 2, wherein A$^1$ and A$^2$ each have a structure of:

—N(R$^1$)—C(R$^2$)(R$^3$)—C(O)— wherein R$^1$ is H; R$^2$ and R$^3$ are each individually selected from H, an optionally substituted alkyl, an optionally substituted cycloalkyl, an optionally substituted heterocycloalkyl, an optionally substituted aryl, or an optionally substituted heteroaryl, or R$^2$ and R$^3$ together form a cycloalkyl structure; or R$^1$ and R$^2$ together form an azacyclic structure.

4. The compound of paragraph 3, wherein
A$^2$ is selected from

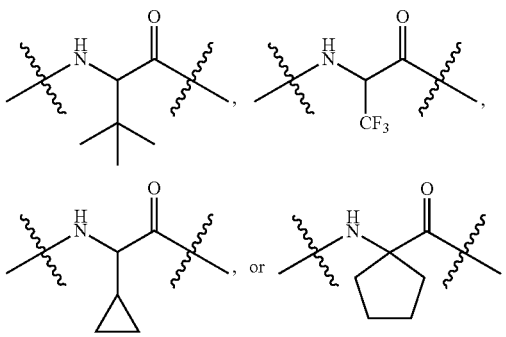

and A$^1$ is selected from:

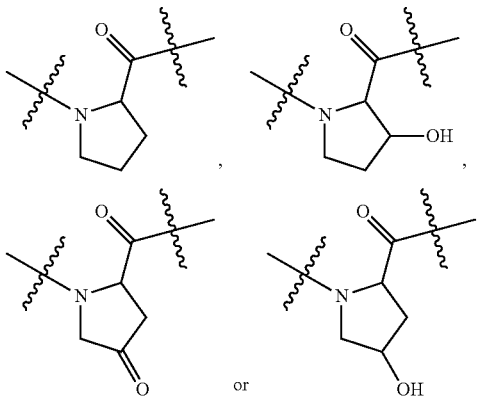

5. The compound of any one of paragraphs 1 to 4, wherein Ar is an optionally substituted phenyl or an optionally substituted pyrindyl, and Ar further includes a carbonyl radical (—C(O)—) that bonds to A$^2$.

6. The compound of any one of paragraphs 1 to 5, wherein Ar is selected from

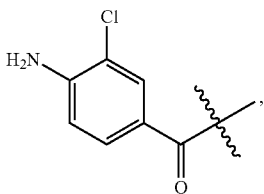

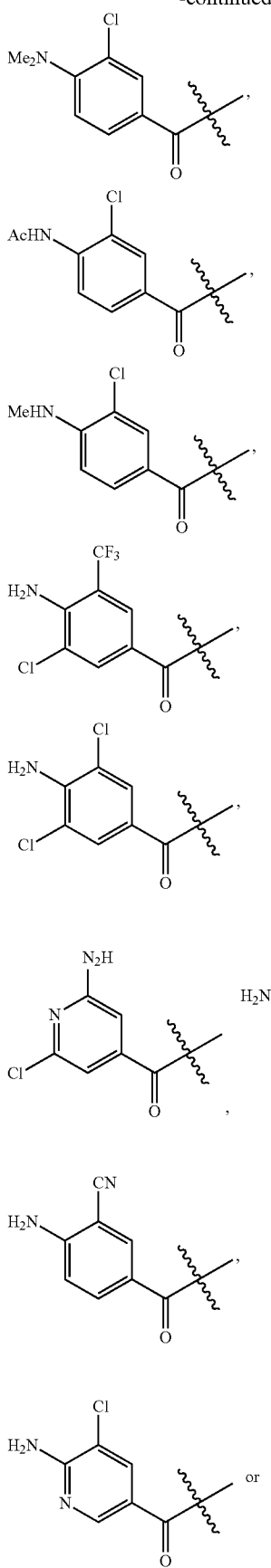

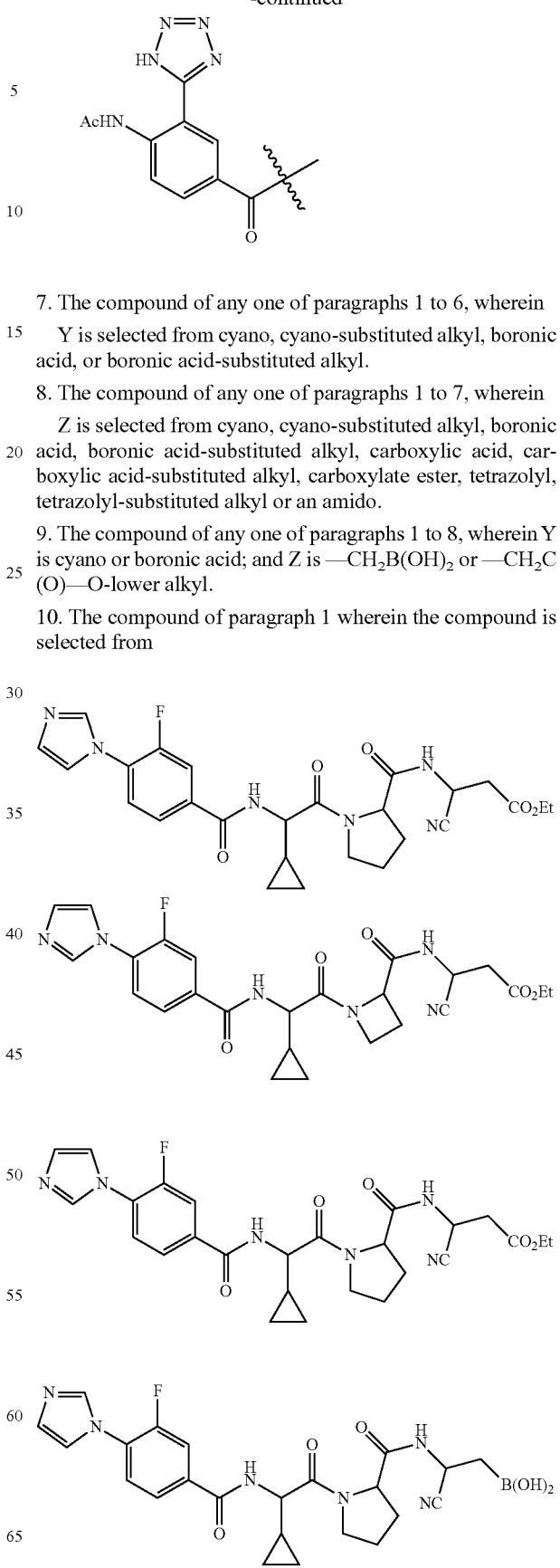

7. The compound of any one of paragraphs 1 to 6, wherein Y is selected from cyano, cyano-substituted alkyl, boronic acid, or boronic acid-substituted alkyl.

8. The compound of any one of paragraphs 1 to 7, wherein Z is selected from cyano, cyano-substituted alkyl, boronic acid, boronic acid-substituted alkyl, carboxylic acid, carboxylic acid-substituted alkyl, carboxylate ester, tetrazolyl, tetrazolyl-substituted alkyl or an amido.

9. The compound of any one of paragraphs 1 to 8, wherein Y is cyano or boronic acid; and Z is —CH$_2$B(OH)$_2$ or —CH$_2$C(O)—O-lower alkyl.

10. The compound of paragraph 1 wherein the compound is selected from

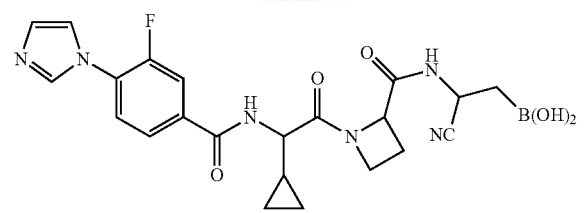
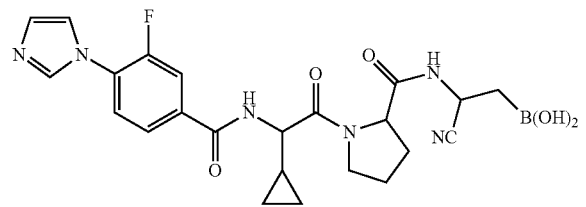
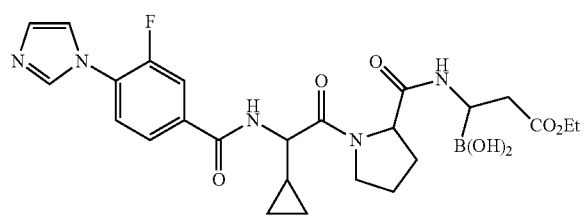
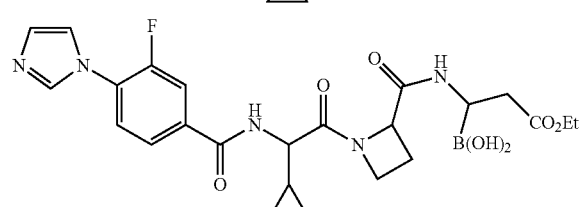
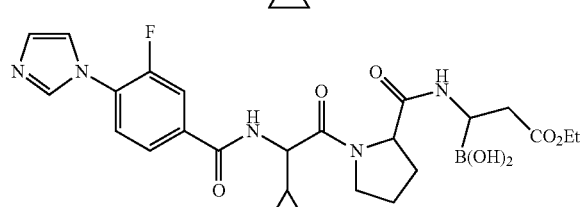
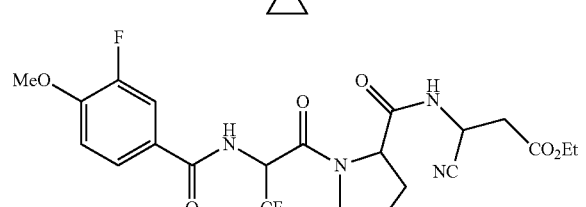
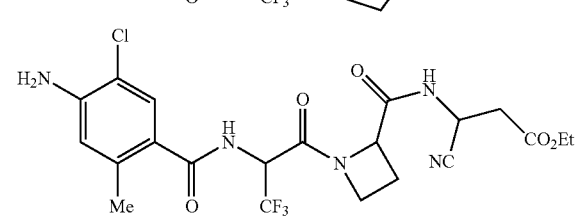
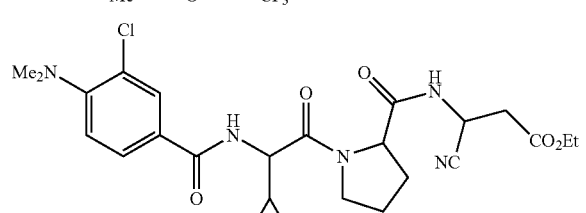
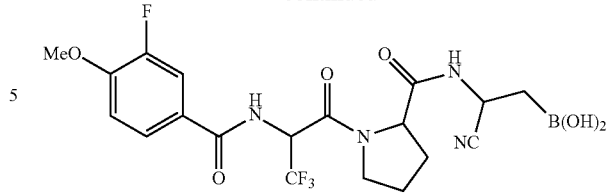
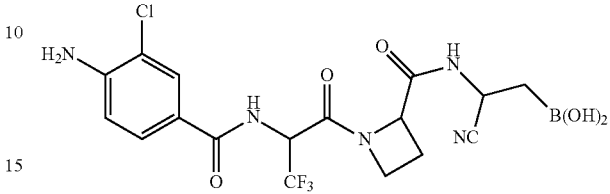
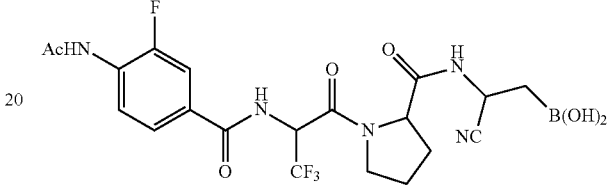
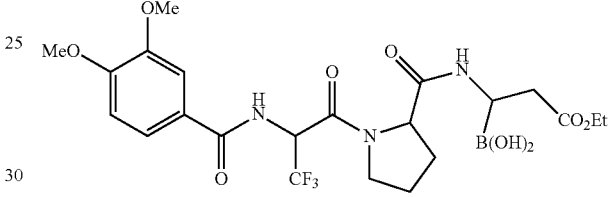
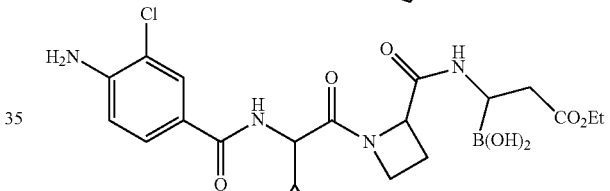
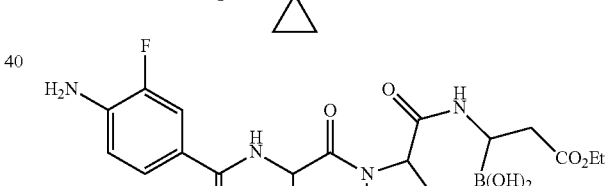
11. A compound, or a pharmaceutically acceptable salt, hydrate or ester thereof, of formula II:
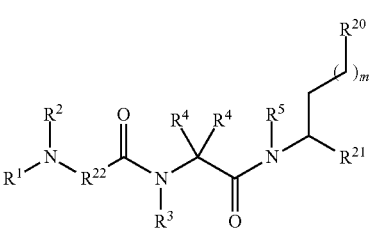
wherein
$R^1$ is H, —C(O)$R^8$, —C(O)C(O)$R^8$, —S(O)$_2R^8$, —S(O)$R^8$, —C(O)O$R^8$, —C(O)N(H)$R^8$, —S(O)$_2$N(H)—$R^8$, —S(O)N(H)—$R^8$, —C(O)C(O)N(H)$R^8$, —C(O)CH=CH$R^8$, —C(O)CH$_2$O$R^8$, —C(O)CH$_2$N(H)$R^8$, —C(O)N($R^8$)$_2$, —S(O)$_2$N($R^8$)$_2$, —S(O)N($R^8$)$_2$, —C(O)C(O)N($R^8$)$_2$, —C(O)CH$_2$N($R^8$)$_2$, —CH$_2R^8$, —CH$_2$-alkenyl-$R^8$, or —CH$_2$-alkynyl-1e;

R² is H and each R⁶ is independently —H, an amino acid side chain, or —R⁸; or R² and R⁶ together with the atoms to which they are bound, form a 3 to 7 membered cyclic or heterocyclic ring system;

R²² is —C(R⁶)₂— or —N(R⁶)—;

R³ is H and each R⁴ is independently —H, an amino acid side chain, or —R⁸; or R³ and R⁴ together with the atoms to which they are bound, form a 3 to 7 membered cyclic or heterocyclic ring system;

R⁵ is —H;

R²¹ is —CN or —C(O)OR⁹;

R²⁰ is —C(O)OR⁹, or a heteroaryl;

R⁹ is —H, alkyl, or —CN; and m is 0 or 1;

provided that at least one of R²⁰ or R²¹ includes —CN.

12. The compound of paragraph 11 having a formula III:

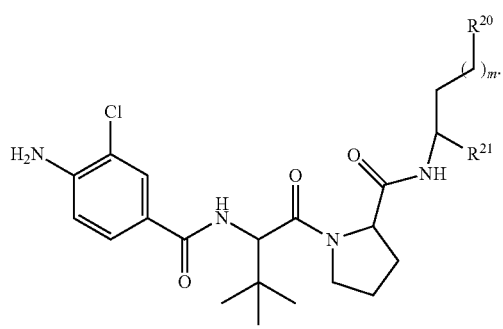

13. The compound of paragraph 12, wherein the compound has the structure of:

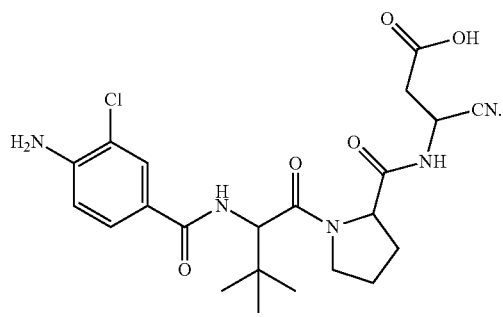 [SMILES: CC(C)(C)C(NC(=O)c1ccc(N)c(Cl)c1)C(=O)N1CCCC1C(=O)NC(C#N)CC(=O)O]

14. The compound of paragraph 12, wherein the compound has the structure of:

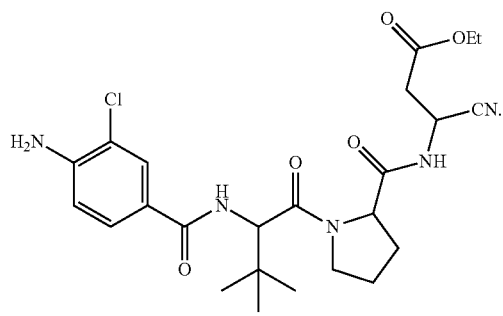

15. The compound of paragraph 12, wherein the compound has the structure of:

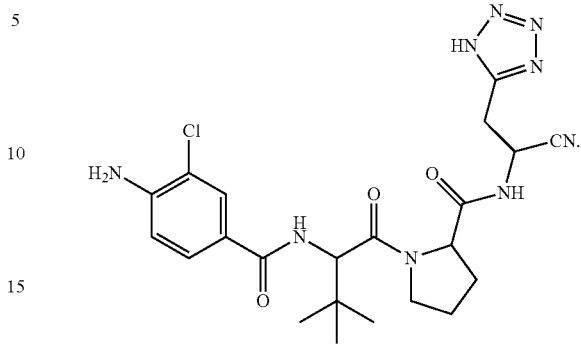

16. The compound of any one of paragraphs 1 to 15, wherein the compound has a caspase inhibition IC₅₀ of less than 100 nM.

17. The compound of any one of paragraphs 1 to 16, wherein the compound has an aqueous solubility of greater than 10 µg/mL, a LogD lower than 5 and a molecular weight of lower than 650 daltons.

18. A pharmaceutical composition comprising a therapeutically effective amount of one or more compounds of any one of paragraphs 1 to 17, and at least one pharmaceutically acceptable additive.

19. A method of treating a caspase-mediated condition in a subject, the method comprising administering to the subject a therapeutically effective amount of one or more compounds of any one of paragraphs 1 to 17.

20. The method of paragraph 19, wherein the caspase-mediated condition is at least one of an IL-1-, apoptosis-, IL-18-, or IFN-γ-mediated disease, an inflammatory disease, an autoimmune disease, a destructive bone disease, a proliferative disease, an infectious disease, or a degenerative disease.

21. The method of paragraph 19 or 20, wherein the caspase-mediated condition is a caspase 1-mediated condition.

22. A method of inhibiting at least one of caspase 1, 4, 5, 8, 9, 10 or 14 activity in a sample, comprising contacting the sample with one or more compounds of any one of paragraphs 1 to 17, whereby the caspase activity is inhibited.

In view of the many possible embodiments to which the principles of the disclosed compounds, compositions and methods may be applied, it should be recognized that the illustrated embodiments are only preferred examples of the invention and should not be taken as limiting the scope of the invention. Rather, the scope of the invention is defined by the following claims.

What is claimed is:

1. A compound, or a pharmaceutically acceptable salt, hydrate or ester thereof, of formula II:

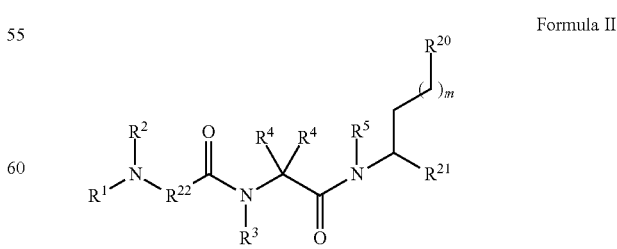

wherein

R¹ is H, —C(O)R⁸, —C(O)C(O)R⁸, —S(O)₂R⁸, —S(O)R⁸, —C(O)OR⁸, —C(O)N(H)R⁸, —S(O)₂N(H)—R⁸,

—S(O)N(H)—R⁸, —C(O)C(O)N(H)R⁸, —C(O)CH=CHR⁸, —C(O)CH₂OR⁸, —C(O)CH₂N(H)R⁸, —C(O)N(R⁸)₂, —S(O)₂N(R⁸)₂, —S(O)N(R⁸)₂, —C(O)C(O)N(R⁸)₂, —C(O)CH₂N(R⁸)₂, —CH₂R⁸, —CH₂-alkenyl-R⁸, or —CH₂-alkynyl-R⁸;

R² is H and each R⁶ is independently —H, or —R⁸; or R² and R⁶ together with the atoms to which they are bound, form a 3 to 7 membered heterocyclic ring system;

R²² is —C(R⁶)₂—;

R³ and a first R⁴ together with the atoms to which they are bound, form a 3 to 7 membered heterocyclic ring system, and a second R⁴ is independently —H or —R⁸;

R⁵ is —H;

each R⁸ is independently alkyl, cycloalkyl, aryl, heteroaryl, heterocyclyl, alkylcycloalkyl, alkylaryl, alkylheteroaryl or alkylheterocyclyl;

R²¹ is —CN or —C(O)OR⁹;

R²⁰ is —C(O)OR⁹, or a heteroaryl;

R⁹ is —H, alkyl, or —CN; and m is 0 or 1;

provided that at least R²¹ is —CN or —C(O)OCN, or R²⁰ is —C(O)OCN.

2. A compound, or a pharmaceutically acceptable salt, hydrate or ester thereof, of formula III:

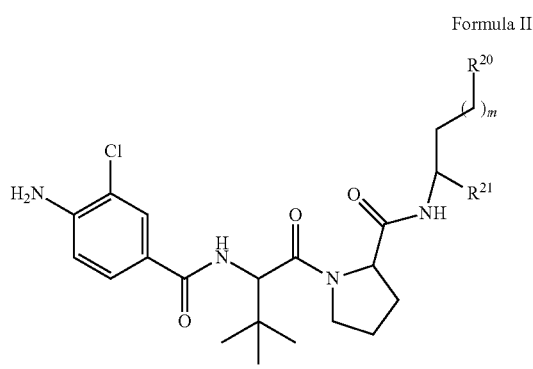

Formula III wherein:
R²¹ is —CN or —C(O)OR⁹;
R²⁰ is —C(O)OR⁹, or a heteroaryl;
R⁹ is —H, alkyl, or —CN; and
m is 0 or 1;
provided that at least R²¹ is —CN or —C(O)OCN, or R²⁰ is —C(O)OCN.

3. The compound of claim 2, wherein the compound has the structure of:

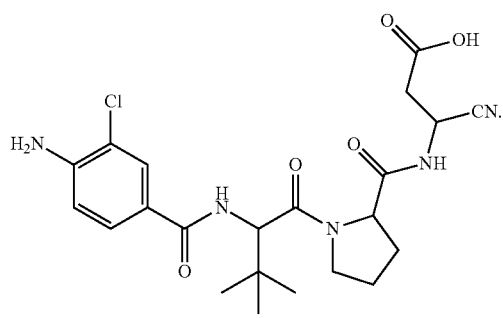 [SMILES: CC(C)(C)C(NC(=O)c1ccc(N)c(Cl)c1)C(=O)N1CCCC1C(=O)NC(C#N)CC(=O)O]

4. The compound of claim 2, wherein the compound has the structure of:

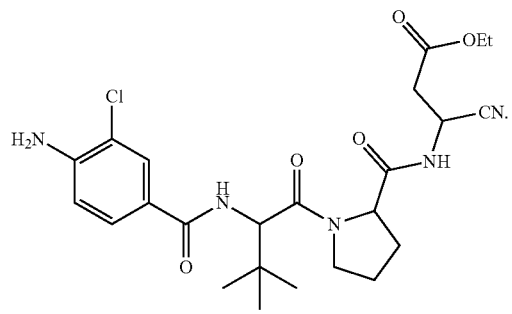 [SMILES: CCOC(=O)CC(C#N)NC(=O)C1CCCN1C(=O)C(NC(=O)c1ccc(N)c(Cl)c1)C(C)(C)C]

5. The compound of claim 2, wherein the compound has the structure of:

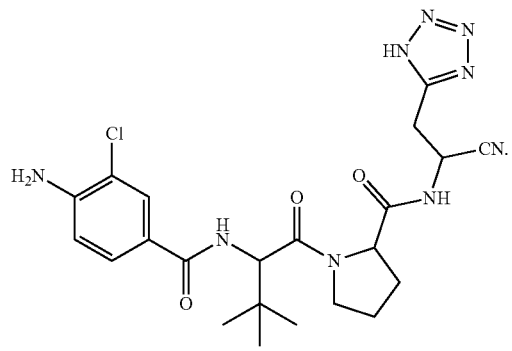 [SMILES: CC(C)(C)C(NC(=O)c1ccc(N)c(Cl)c1)C(=O)N1CCCC1C(=O)NC(C#N)Cc1nnn[nH]1]

6. The compound of claim 1, wherein the compound has a caspase inhibition IC₅₀ of less than 100 nM.

7. The compound of claim 1, wherein the compound has an aqueous solubility of greater than 10 μg/mL, a LogD lower than 5 and a molecular weight of lower than 650 daltons.

8. A pharmaceutical composition comprising a therapeutically effective amount of one or more compounds of claim 1, and at least one pharmaceutically acceptable additive.

9. A pharmaceutical composition comprising a therapeutically effective amount of the compound of claim 4, and at least one pharmaceutically acceptable additive.

10. The compound of claim 1, wherein the compound is selected from

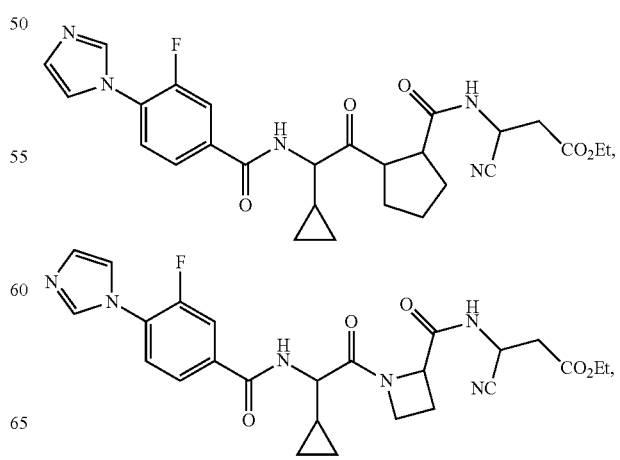

-continued

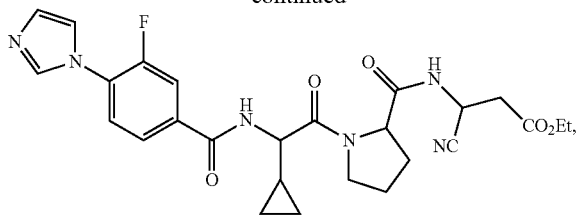

11. A pharmaceutical composition comprising a therapeutically effective amount of the compound of claim 3, and at least one pharmaceutically acceptable additive.

12. The compound of claim 1, wherein $R^1$ is —C(O)$R^8$, wherein $R^8$ is substituted phenyl.

13. The compound of claim 1, wherein $R^1$ is —C(O)$R^8$, wherein $R^8$ is 4-amino-3-chlorophenyl.

14. The compound of claim 1, wherein $R^3$ and the first $R^4$ together form a 4-membered or 5-membered heterocyclic ring system.

15. The compound of claim 1, wherein $R^{21}$ is cyano.

16. A compound, or a pharmaceutically acceptable salt, hydrate or ester thereof, of formula II:

Formula II wherein
$R^1$ is —C(O)$R^8$, wherein $R^8$ is substituted phenyl;
$R^2$ is H and each $R^6$ is independently —H, or —$R^8$; or $R^2$ and $R^6$ together with the atoms to which they are bound, form a 3 to 7 membered heterocyclic ring system;
$R^{22}$ is —C($R^6$)$_2$—;
$R^3$ is H and each $R^4$ is independently —H or —$R^8$; or $R^3$ and $R^4$ together with the atoms to which they are bound, form a 3 to 7 membered heterocyclic ring system;
$R^5$ is —H;
each $R^8$ is independently alkyl, cycloalkyl, aryl, heteroaryl, heterocyclyl, alkylcycloalkyl, alkylaryl, alkylheteroaryl or alkylheterocyclyl;
$R^{21}$ is —CN or —C(O)O$R^9$;
$R^{20}$ is —C(O)O$R^9$, or a heteroaryl;
$R^9$ is —H, alkyl, or —CN; and
m is 0 or 1;
provided that at least $R^{21}$ is —CN or —C(O)OCN, or $R^{20}$ is —C(O)OCN.

* * * * *